US011950956B1

(12) United States Patent
Willey et al.

(10) Patent No.: US 11,950,956 B1
(45) Date of Patent: Apr. 9, 2024

(54) PIEZOELECTRIC MICROMACHINED ULTRASONIC TRANSDUCER SENSOR APPARATUSES, SYSTEMS, AND METHODS

(71) Applicant: RFNAV Inc., Glenelg, MD (US)

(72) Inventors: Jefferson Willey, Glenelg, MD (US); Richard Pavek, Marble Falls, TX (US); James Schoenduve, Hansville, WA (US)

(73) Assignee: RFNAV Inc., Glenelg, MD (US)

( * ) Notice: Subject to any disclaimer, the term of this patent is extended or adjusted under 35 U.S.C. 154(b) by 0 days.

(21) Appl. No.: 18/146,369

(22) Filed: Dec. 24, 2022

Related U.S. Application Data

(60) Provisional application No. 63/267,432, filed on Feb. 2, 2022, provisional application No. 63/266,320, filed on Dec. 31, 2021.

(51) Int. Cl.
*A61B 8/00* (2006.01)
*B06B 1/06* (2006.01)
(Continued)

(52) U.S. Cl.
CPC ........ *A61B 8/4494* (2013.01); *B06B 1/0633* (2013.01); *G01N 29/2437* (2013.01); *H10N 30/2047* (2023.02); *B06B 1/00* (2013.01)

(58) Field of Classification Search
CPC ....... A61B 8/4444; A61B 8/4494; B06B 1/00; B06B 1/0215; B06B 1/04–045;
(Continued)

(56) References Cited

U.S. PATENT DOCUMENTS 10,273,797 B2  4/2019  Li
10,927,669 B2  2/2021  Coates
(Continued)

FOREIGN PATENT DOCUMENTS

GB        2593477 A  *  9/2021  ........... B06B 1/0215
WO   WO-2021119182 A1 *  6/2021  ............... G01H 9/00

OTHER PUBLICATIONS

Kiyono et al, Determination of full piezoelectric complex parameters using gradient-based optimization algorithm, Smart Mater. Struct. 25 (2016) 025019 (18pp) (Year: 2016).*
(Continued)

*Primary Examiner* — David L Singer
(74) *Attorney, Agent, or Firm* — Nemphos Braue LLC; Michael Antone

(57) ABSTRACT

Apparatuses, systems, and methods include a PMUT mechanically coupled to, and electrically isolated from, a receive sensor via a common flexible membrane. The receive sensor may be an optical sensor or a receive only PMUT providing a feedback signal based on a received waveform, $V_{RO}(t)$, to modify the drive voltage $V_d(t)$ of the PMUT. The feedback signal may be used to modify the drive voltage $V_d(t)$ of the PMUT to shorten the ring-down period and may be based on the received waveform, $V_{RO}(t)$, and a desired receive waveform, $V_{ROD}(t)$, which may be selected to optimize one or more of Q, bandwidth, resonant frequency, and spectral content of the drive voltage $V_d(t)$. The drive voltage $V_d(t)$ may be modified to a minimize a difference between $V_{RO}(t)$, and a desired receive waveform, $V_{ROD}(t)$, or a closed loop weighted ($\alpha$, $\beta$) sum of the energy of $V_{RO}(t)$ and the blind zone duration.

20 Claims, 26 Drawing Sheets

PMOUT embodiment as a hybrid PMUT and an RO optical sensor

(51) Int. Cl.
*G01N 29/24* (2006.01)
*H10N 30/20* (2023.01)
*B06B 1/00* (2006.01)

(58) Field of Classification Search
CPC .. B06B 1/06–0685; B06B 2201/55–56; G01H 9/00; G01H 9/004; G01H 9/006; G01N 29/0654; G01N 29/2437; G01N 29/245; G01N 29/343; G01N 29/348; H10N 30/2047
See application file for complete search history.

(56) References Cited

U.S. PATENT DOCUMENTS

| | | | |
|---|---|---|---|
| 2016/0206288 A1* | 7/2016 | Choi | A61B 8/5207 |
| 2016/0380640 A1* | 12/2016 | Boser | H03L 7/00 367/13 |
| 2018/0246193 A1* | 8/2018 | Kline | G01S 7/521 |
| 2020/0162156 A1* | 5/2020 | Parker | H01L 31/022416 |
| 2020/0174116 A1* | 6/2020 | Toda | G01S 15/102 |
| 2020/0292684 A1* | 9/2020 | Passoni | G01S 7/524 |
| 2022/0326185 A1* | 10/2022 | Kline | A47L 9/2852 |

OTHER PUBLICATIONS

Pop et al, Novel pMUT-based Acoustic Duplexer for Underwater and Intrabody Communication, 2018 IEEE International Ultrasonics Symposium (IUS) (Year: 2018).*

Leinders et al, A sensitive optical micro-machined ultrasound sensor (OMUS) based on a silicon photonic ring resonator on an acoustical, Nature Scientific Reports (Year: 2015).*

Litslink, An Introduction to Machine Learning Algorithms, Retrieved from the Internet: <URL: https://litslink.com/blog/an-introduction-to-machine-learning-algorithms#:~:text=Q-Learning > (Year: 2019).*

Pala et al, Improved Ring-Down Time and Axial Resolution of PMUTS Via a Phase-Shift Excitation Scheme, IEEE MEMS 2021 Virtual Conference Jan. 25-29, 2021 (Year: 2021).*

Agarwal, R., et al. "Fabrication of vertical mirrors using plasma etch and KOH: IPA polishing." Journal of Micromechanics and Microengineering 17, No. 1 (2006): 26.

Benayad, A., et al. "Temperature dependence of piezoelectric properties of PMN-PT and PZN-PT single crystals." In Journal de Physique IV (Proceedings), vol. 126, pp. 53-57. EDP sciences, 2005.

Chuang, Y., et al. "Application of the inclined exposure and molding process to fabricate a micro beam-splitter with nanometer roughness." Microsystem technologies 19, No. 3 (2013): 461-470.

Deng, Y., et al. "Coherence properties of different light sources and their effect on the image sharpness and speckle of holographic displays." Scientific reports 7, No. 1 (2017): 1-12.

Dorrer, C. "Temporal van Cittert-Zernike theorem and its application to the measurement of chromatic dispersion." JOSA B 21, No. 8 (2004): 1417-1423.

Eovino, B. E., et al. "Ring shaped piezoelectric micromachined ultrasonic transducers (PMUT) with increased pressure generation." In Proceedings of the Solid-State Sensors, Actuators Microsystems Workshop, Hilton Head Island, SC, USA, pp. 5-9. 2016.

Feeney, A., et al. "The influence of air pressure on the dynamics of flexural ultrasonic transducers." Sensors 19, No. 21 (2019): 4710.

Feng, J., et al. "A three-dimensional silicon nitride polarizing beam splitter." IEEE Photonics Technology Letters 26, No. 7 (2014): 706-709.

Grote, R., et al. "Single-mode optical waveguides on native high-refractive-index substrates." APL Photonics 1, No. 7 (2016): 071302.

Hernandez, A., et al. "Reduction of blind zone in ultrasonic transmitter/receiver transducers." Sensors and Actuators A: Physical 133, No. 1 (2007): 96-103.

Jiang, X., et al. "Monolithic ultrasound fingerprint sensor." Microsystems & Nanoengineering 3, No. 1 (2017): 1-8.

Kim, J., et al., "10 MHz thin-film PZT-based flexible PMUT array: Finite element design and characterization." Sensors 20, No. 15 (2020): 4335.

Kusano, Y., et al., "Effects of DC bias tuning on air-coupled PZT piezoelectric micromachined ultrasonic transducers." Journal of Microelectromechanical Systems 27, No. 2 (2018): 296-304.

Lillicrap, T., et al., "Continuous control with deep reinforcement learning." arXiv preprint arXiv:1509.02971 (2015).

Liu, X., et al. "Reducing ring-down time of pMUTs with phase shift of driving waveform." Sensors and Actuators A: Physical 281 (2018): 100-107.

Lu, Y., et al. "Piezoelectric micromachined ultrasonic transducers with increased coupling coefficient via series transduction." In 2015 IEEE International Ultrasonics Symposium (IUS), pp. 1-4. IEEE, 2015.

Luoto, H., et al. "MEMS on cavity-SOI wafers." Solid-State Electronics 51, No. 2 (2007): 328-332.

Massimino, G., et al. "On the effects of package on the PMUTs performances—multiphysics model and frequency analyses." Micromachines 11, No. 3 (2020): 307.

Przybyla, R. Ultrasonic 3D rangefinder on a chip. PhD Thesis. University of California, Berkeley, 2013.

Ross, G., et al. "The impact of residual stress on resonating piezoelectric devices." Materials & Design 196 (2020): 109126.

Sadeghpour, S., et al. "Design and fabrication of a piezoelectric micromachined ultrasound transducer (pMUT) array for underwater communication." In Proceedings of Meetings on Acoustics ICU, vol. 38, No. 1, p. 045006. Acoustical Society of America, 2019.

Salajeghe, S., et al. "Nonlinear analysis of thermoelastic damping in axisymmetric vibration of micro circular thin-plate resonators." Applied Mathematical Modelling 36, No. 12 (2012): 5991-6000.

Uenishi, Y., et al. "Micro-opto-mechanical devices fabricated by anisotropic etching of (110) silicon." Journal of Micromechanics and Microengineering 5, No. 4 (1995): 305.

Wang, T., et al. "Zero-bending piezoelectric micromachined ultrasonic transducer (pMUT) with enhanced transmitting performance." Journal of Microelectromechanical Systems 24, No. 6 (2015): 2083-2091.

Wu, Z., et al. "A novel transfer function based ring-down suppression system for PMUTs." Sensors 21, No. 19 (2021): 6414.

Eovino, B. Ring-shaped and dual-electrode bimorph piezoelectric micromachined ultrasonic transducers, PhD Thesis, University of California, Berkeley, 2018.

* cited by examiner

Top View

Bottom View minus Supporting Elastic Membrane

| Blind Period / 20 Cycle Tx Period | # Cycles in Blind Zone at Resonant Frequency | Blind Zone Period (usecs) | Resonant Frequency (MHz) | Anti-Ring Down Apparatus of FIG. 2, Method |
|---|---|---|---|---|
| 1.54 | 30.8 | 30.8 | 1.00 | Open Loop, T/R RO PMUT, No Ring Down Mitigation FIG. 6 |
| 0.70 | 14.0 | 14.0 | 1.00 | Open Loop, T/R RO PMUT, Inverse Transfer Function |
| 0.89 | 17.7 | 13.6 | 1.30 | Open Loop, T/R RO PMUT, DC Bias |
| 0.50 | 10.1 | 10.1 | 1.00 | Open Loop, T/R RO PMUT, Phase Shift |
| 0.07 | 1.3 | 1.2 | 1.13 | Closed Loop, T/R RO PMUT, RO Energy Minimization FIGs. 13-15 |

FIG. 16

PIEZOELECTRIC MICROMACHINED ULTRASONIC TRANSDUCER SENSOR APPARATUSES, SYSTEMS, AND METHODS

CROSS-REFERENCE TO RELATED APPLICATIONS

The application claims the benefit of and priority to US Provisional Patent Application Serial Nos. 63/266,320 filed Dec. 31, 2021 and 63/267,432, filed Feb. 2, 2022, each of which is incorporated herein by reference in its entireties.

BACKGROUND OF THE INVENTION

Field of the Invention

The present invention generally relates to ultrasonic imaging with micromachined ultrasonic transducers. More specifically, the present invention is directed to sensors utilizing piezoelectric micromachined ultrasonic transducers for short range ultrasonic imaging including medical imaging and fingerprint scanning and identification applications.

Background

Low cost piezoelectric micromachined ultrasonic transducers (PMUTs) are employed in numerous applications including fingerprint ID and medical imaging sensors. The sensors utilize pulse echo and chirp frequency waveforms to estimate object distance via time-of-flight detection, estimate relative motion, and form images.

Unfortunately, PMUT sensors have limited dynamic range and sensitivity at short range compromising small object detection. In addition, the application of external pressure to the sensor, such as when a fingertip is pressed hard against a sensor can degrade the performance of the PMUT resulting in image distortion.

Despite these shortcomings, PMUT sensors often are the preferred choice for their low power, size, cost, and fabrication ease for many applications noted above. As such, there remains a continuing need for PMUT sensors capable of performing detection and imaging at close range with improved accuracy.

BRIEF SUMMARY OF THE INVENTION

Piezoelectric Micromachined Ultrasonic Transducer (PMUT) apparatuses, systems, and methods of the present invention include one or more PMUT mechanically coupled to, and electrically isolated from, a receive sensor via a common flexible membrane with the receive sensor providing a feedback signal based on a received waveform, $V_{RO}(t)$, to modify the drive voltage $V_d(t)$ of the at least one PMUT. The receive sensor may be an optical sensor or a PMUT operating in receive only mode. In various embodiments, the PMUT may be a transceiver operating in half-duplex mode and/or in transmit-only mode. In various embodiments, the feedback signal from the receive sensor is used to modify the drive voltage $V_d(t)$ of the PMUT to shorten the ring-down period of the PMUT. The feedback signal may be based on the received waveform, $V_{RO}(t)$, and a desired receive waveform, $V_{ROD}(t)$. The desired receive waveform, $V_{ROD}(t)$, may be selected to optimize one or more of Q, bandwidth, resonant frequency, and spectral content of the drive voltage $V_d(t)$. The drive voltage $V_d(t)$ may be modified to achieve one or more design objectives, such as to minimize a difference between $V_{RO}(t)$, and a desired receive waveform, $V_{ROD}(t)$, or a closed loop weighted ($\alpha$, $\beta$) sum of the energy of $V_{RO}(t)$ and the blind zone duration. Various techniques may be used to modify the drive voltage $V_d(t)$ including, but not limited to, gradient methods and model free reinforcement machine learning methods.

In various embodiments, the receive sensor is a PMUT operating in receive only mode, $PMUT_{RO}$, where the PMUT and the $PMUT_{RO}$ are physically and electrically separated on the common flexible membrane. For example, the positive and negative electrodes of one of PMUT and the $PMUT_{RO}$ may be designed to surround the other of the at least one PMUT and the $PMUT_{RO}$ positive and negative electrodes. The electrodes may be configured to provide a symmetrical layout out, such as with a ring and disc configuration, or asymmetrically.

In addition, the apparatuses may include a switch to enable one set of the positive and negative electrodes to operate as the transceiver or transmit-only PMUT and the other set of positive and negative electrodes to operate as the $PMUT_{RO}$ in a first switch position and the one set of the positive and negative electrodes to operate as the $PMUT_{RO}$ and the other set of positive and negative electrodes to operate as the transceiver or transmit-only PMUT in a second switch position.

In various embodiments, the receive sensor is an optical vibration sensor including one or more optical waveguides and the received waveform, $V_{RO}(t)$, is based on the physical displacement of the optical waveguides. The physical displacement of the optical waveguide may be measured based on one of optical time of flight and interference pattern intensity profile measurements. The optical waveguide may be dry etched into a silicon substrate or produced in other manners suitable for PMUT manufacturing and may be positioned in a plane parallel to the PMUT.

Apparatuses, systems, and methods of the present invention may be employed reduce the blind zone, or post transmission ring-down period, to observe close range objects with piezoelectric micromachined ultrasonic transducers (PMUT) based sensors. Various embodiments of the invention integrate an in-vivo full duplex transducer comprised of two joint PMUT sub-components, or one PMUT sub-component with an optical sensor sub-component, on a common mechanically coupled flexible membrane. A transmit only PMUT and a mechanically coupled receive only PMUT or optical sensor, with closed loop feedback signal from receive sensor to transmit PMUT, may be used to suppress membrane displacement oscillation and reduces the duration of the acoustic ringing, enabling detection and imaging of objects at short ranges. The apparatus also allows optimization of the transmit waveform's Q, bandwidth, resonant frequency, and spectral content. The invention permits operation in the PMUT's non-linear membrane displacement compression region as well as in the presence of unknown component variances, unknown temperature, and unknown external pressure. The apparatuses and methods are suitable for low-cost, low-power, volume production utilizing microfabrication methods and integrated circuits.

Accordingly, the present invention addresses the need for high fidelity ultrasonic imaging at close range such as fingerprint ID sensors and dermatological imaging applications.

BRIEF DESCRIPTION OF THE DRAWINGS

The accompanying drawings are included for the purpose of exemplary illustration of various aspects of the present invention to aid explanation and understanding, and not for purposes of limiting the invention, wherein:

FIG. 16 compares an exemplary closed-loop ring-down period minimization for a full-duplex joint PMUT embodiment of FIG. 2, with open loop embodiments;

DETAILED DESCRIPTION OF THE INVENTION

Figure 1:
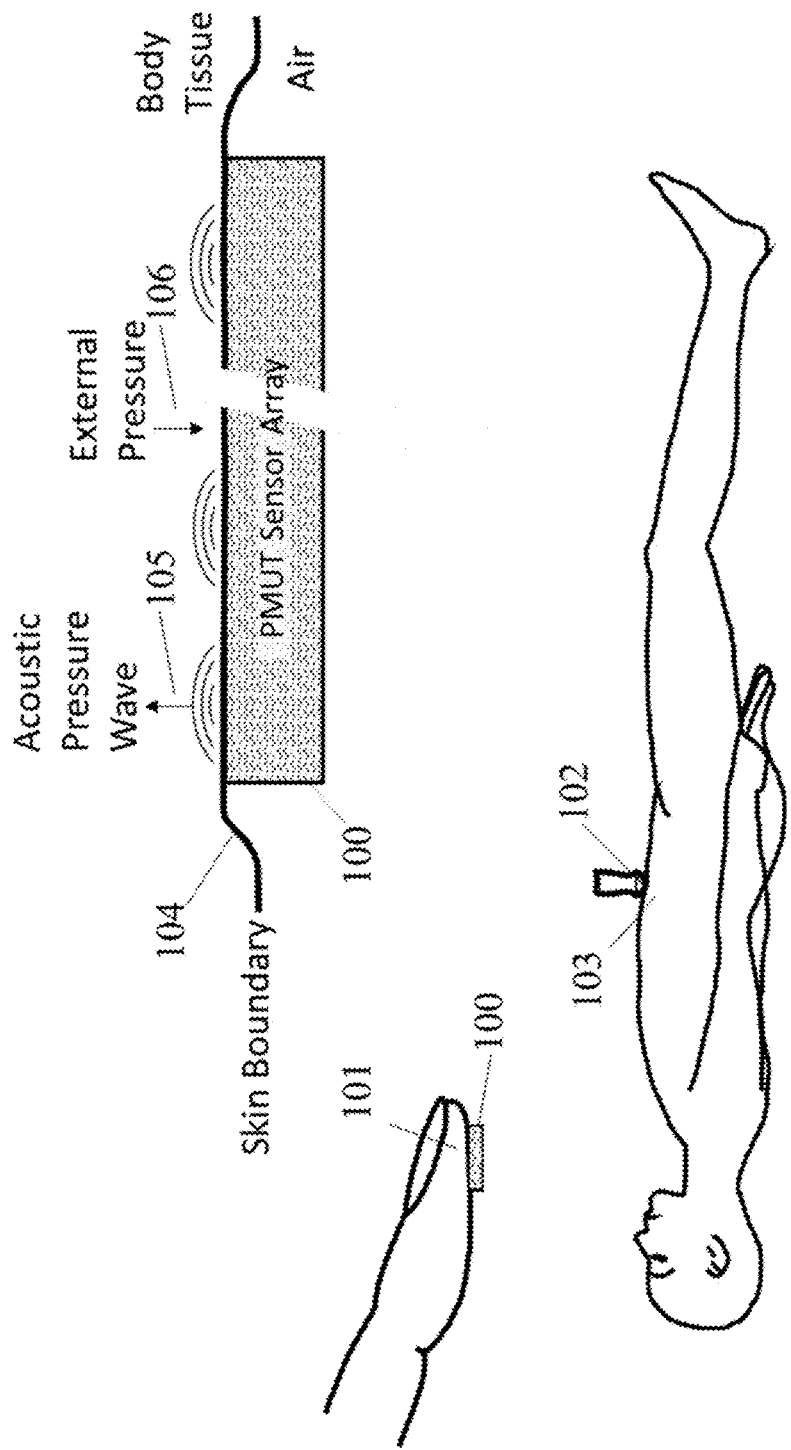
FIG. 1 shows close range fingerprint sensor and medical imaging applications utilizing PMUT based sensors.

Close range applications of PMUT based sensors 100 102 illustrated in FIG. 1, include fingerprint imaging 101 and medical imaging of the skin surface 104 and sub-dermal layers 103. In such applications the acoustic pressure waves 105 generated by the PMUT transducers are almost immediately reflected back to the transducers by the skin adjacent to the PMUT sensor array. Further, post-transmission, the flexing membranes have an extended relaxation or ring-down or range blind-zone, at the PMUT's mechanical resonant frequency that degrades, else makes impossible, the observation of echoes from nearby objects.

Apparatuses, systems, and methods of the present invention mitigate the membrane ring-down problems by introducing simultaneous transmission and reception, or full duplex transduction, enabling the reduction of the blind zone period thereby supporting object detection at closer range. The reduced energy in the ring down artifacts increases dynamic range and contrast in the received signal and derived image products.

Figure 2:
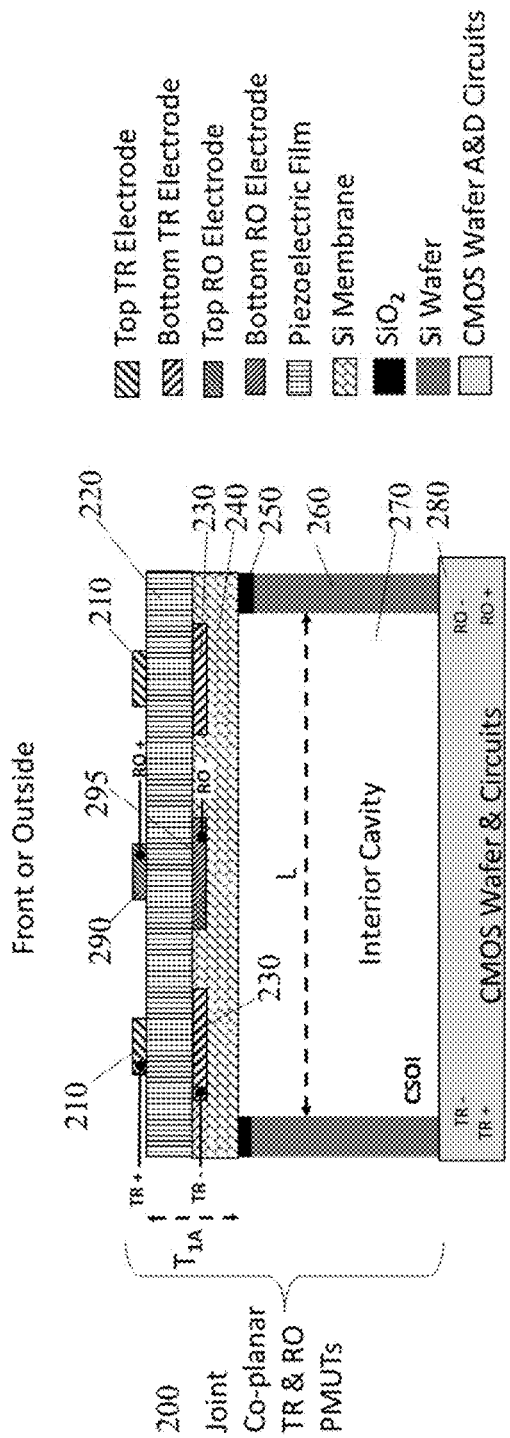
FIG. 2 shows exemplary joint PMUT embodiments comprised of a transmit only PMUT sub-component and a receive only PMUT sub-component mechanically coupled to common membrane in co-planar position and its components.

In various embodiments, a single joint PMUT that supports full duplex transduction may be employed, as shown in FIG. 2, which is not to scale. A flexible piezoelectric film 220 with top and bottom electrodes 210 230 290 295 is formed on a pre-etched cavity silicon-on-insulator (CSOI) 270 wafer 260 with connections to transmit/receive (TR) and receive-only (RO) analog and digital circuits in a lower CMOS wafer 280. A common piezoelectric film supports both TR 210 230 and RO 290 295 PMUT sub-components in a co-planar position layered above a flexible, typically Si, layer 240. The joint membrane stack is layered above a ring of stiff mechanical supports 250, typically $SiO_2$, which in turn is layered above a typical Si wafer, 260. Electrode geometry is optimized to maximize mechanical coupling and minimize electrical cross-talk between the TR and RO PMUT subcomponents while maintaining the membrane's unimorph bending characteristic at resonance. An outer electrode ring pair 210 230 is coupled to the TR circuit and the inner electrode disc pair 290 295 is coupled to the RO circuit. While the two PMUT sub-components are fabricated as a single joint PMUT device on a common piezoelectric layer, it is convenient to separately refer to each as a TR PMUT and an RO PMUT.

Figure 3:
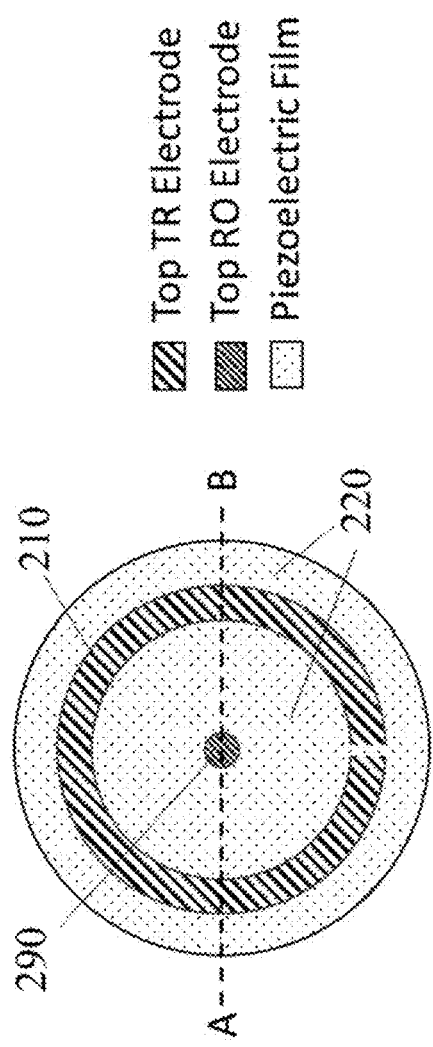
FIG. 3 shows a top view of exemplary joint PMUT embodiments comprised of a transmit only PMUT and a receive only PMUT mechanically coupled to common membrane in co-planar position and its components.
Figure 4:
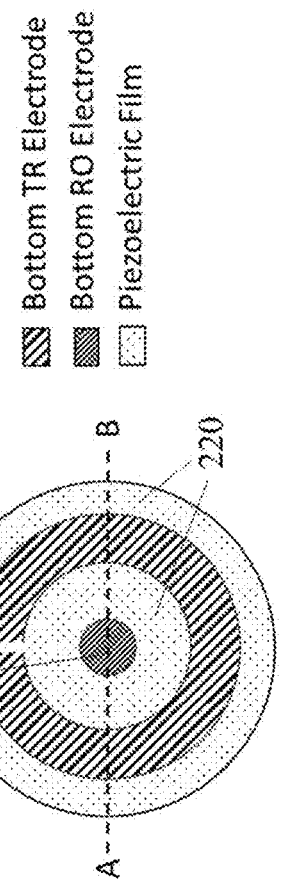
FIG. 4 shows a bottom view, without a supporting elastic layer, of exemplary joint PMUT embodiments comprised of a transmit only PMUT and a receive only PMUT mechanically coupled to common membrane in co-planar position and its components.

Top and bottom views of the joint PMUT device from FIG. 2 are shown in FIG. 3 and FIG. 4. In the top view of FIG. 3, the top TR ring shaped electrode 210 is in co-planar position with the top disc shaped RO electrode 290 on top side of the piezoelectric film 220. In the bottom view of FIG. 4, the bottom TR ring shaped electrode 230 is in co-planar position with the bottom disc shaped RO electrode 295 on the bottom side of the piezoelectric film 220.

The outer parallel rings of top and bottom electrodes 210 230 forms the TR PMUT function. The inner pair of top and bottom disc shaped electrodes 290 295 forms the RO PMUT function. Trace and vias connecting electrodes to transmitter and receiver not shown. Wire trace routing and vias for connection to TR and RO analog and digital circuits in the lower CMOS wafer 280 are also not shown.

The joint TR RO PMUT flexible membrane thickness, $T_{1A}$, FIG. 2 and radii of each electrode pair are designed to optimize Q, bandwidth, and minimize electric field crosstalk between TR electrodes and RO electrodes. The resonant frequency of the joint PMUT is proportional to $T_{1A} L^{-2}$, where L is the diameter defined by the membrane's ring-shaped mechanical support 250 across the interior cavity 270.

The designation of the outer ring-shaped electrodes as the TR piezoelectric transducer and the inner circular disc-shaped electrodes as the RO piezoelectric sensor has performance advantages. When the transmitter is coupled to the outer ring-shaped electrodes to constitute the TR transducer, the effective aperture is larger with more piston-like membrane motion resulting in increased acoustic pressure and directivity or narrower beamwidths. Coupling the inner circular-disc shaped electrodes to the receiver to constitute the RO piezoelectric sensor, allows optimization of the disc radius to trade capacitive coupling between TR and RO PMUTs and receiver sensitivity.

On the other hand, phase steerable joint PMUT arrays whose field-of-view requires wide azimuthal and elevation angles extents benefit by having the transmitter drive the inner disc-shaped electrodes. The individual disc-shaped PMUT with its smaller effective aperture has a wider beamwidth compared to the larger diameter ring-shaped PMUT.

Figure 5:
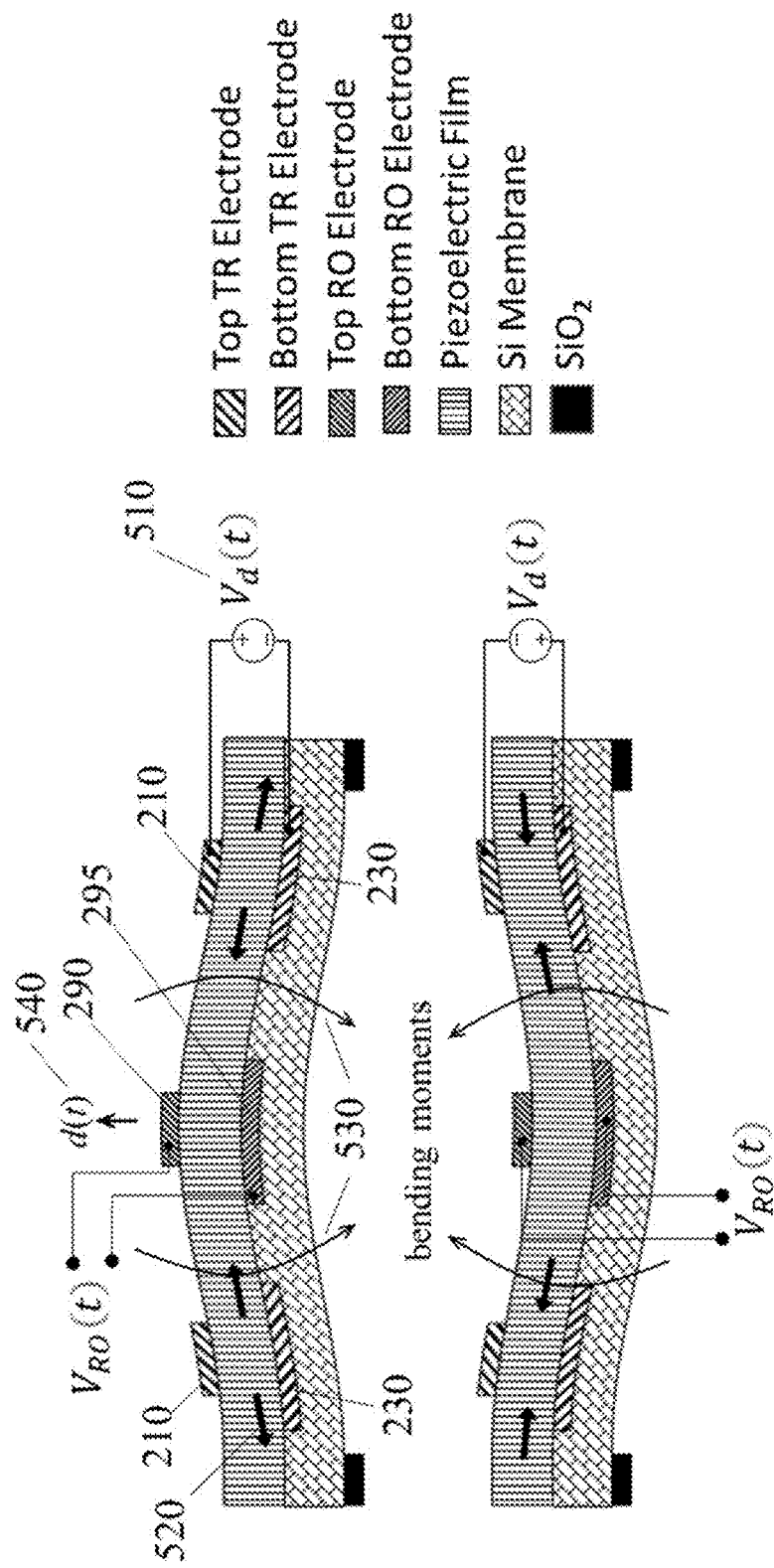
FIG. 5 depicts full-duplex PMUT transduction between electrical and mechanical domains.

PMUT full duplex transduction is illustrated in FIG. 5. During transmission, a drive voltage $V_d(t)$ 510 is introduced across the top 210 and bottom 230 outer ring electrodes forming a local vertical electric field inside the piezoelectric layer. The vertical electric field induces an in-plane (31-mode), orthogonal, piezoelectric stresses 520, resulting in bending moments 530. The stress is relieved by vertical membrane displacement, d(t) 540. The vertically displaced bent piezoelectric layer results in a local electric field formation between the inner top 290 and bottom 295 disc electrodes and appears as a voltage potential $V_{RO}(t)$ 510, across the same inner electrode pair.

During transmission, when $V_d(t)$ is active, the voltage potential $V_{RO}(t)$ to be simultaneously available. The $V_{RO}(t)$ signal provides an independent measurement of the actual vertical membrane displacement d(t).

On receive, $V_d(t)$ is removed. The in-plane stress from any piezoelectric membrane displacement relative to its neutral position induces vertical electric field formation which manifests as a voltage potential $V_{RO}(t)$ across the inner disc top and bottom electrodes 290 295 as well as the outer ring top and bottom electrodes 210 230.

During nominal transmission, membrane displacement, and $V_{RO}(t)$, is a function of the joint PMUT's response to drive voltage $V_d(t)$ with external pressure 106, close-by reflections and other contributing factors. During the nominal ring-down period the membrane displacement function, and $V_{RO}(t)$, are a superposition of the relaxation process at resonance with contributions from static external pressure, close-by acoustic pressure wave reflections and other factors.

One motivation for the full-duplex PMUT embodiment of FIG. 2 arises from the difficulty in predicting and cancelling the ring-down response for practical PMUT sensors.

In typical applications of PMUT based sensors, the transducers are driven hard, with large magnitude drive $V_d(t)$ transmit waveforms, to maximize acoustic power transmission into the coupled medium. In this realm, the PMUT response departs markedly from a linear model, inducing compression and harmonics whose affects, post transmission, make the prediction of the ring-down response difficult.

Figure 6:
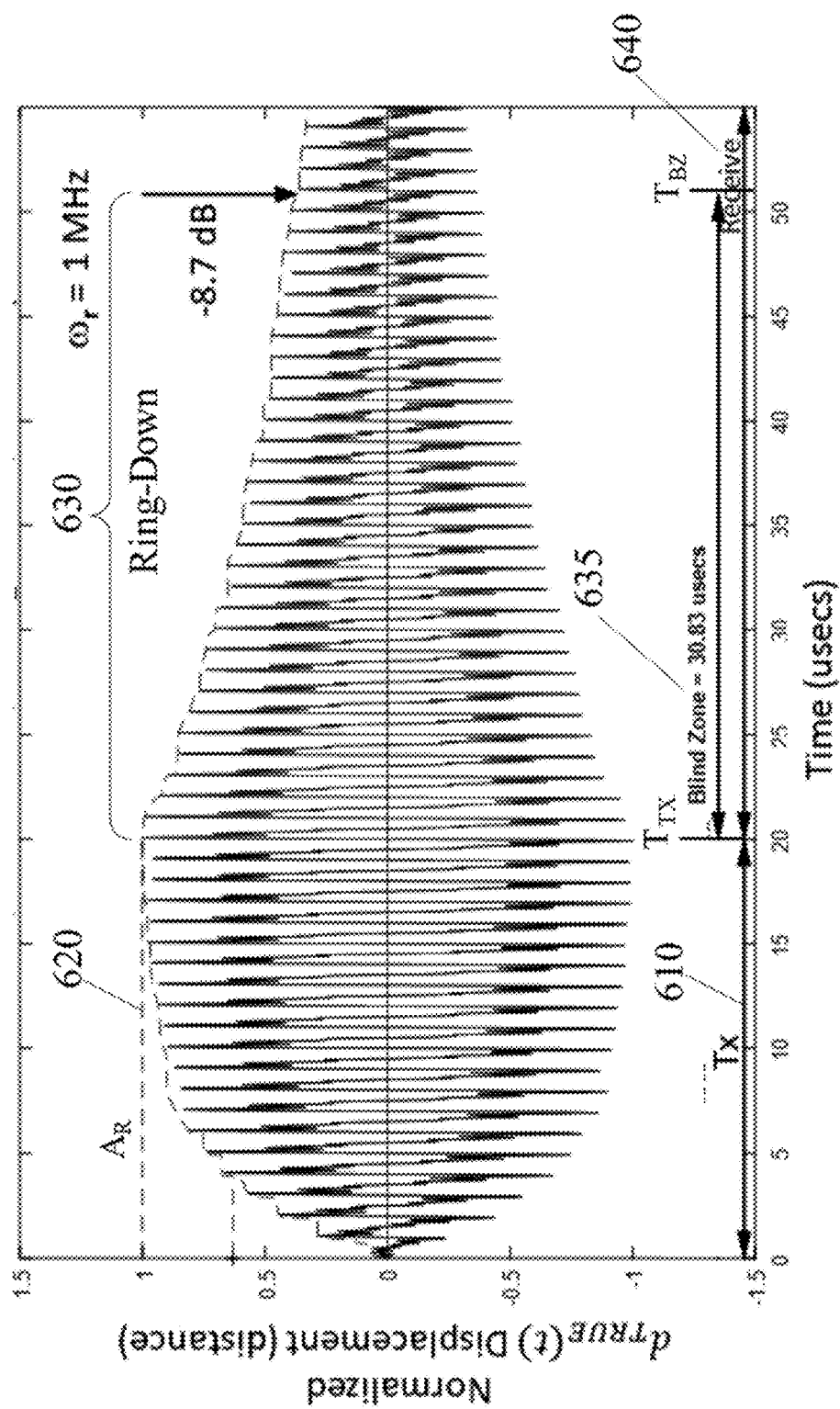
FIG. 6 illustrates an exemplary normalized displacement function for the exemplary joint PMUT embodiment of FIG. 2 with large magnitude drive signals inducing compression on transmit.

FIG. 6 illustrates a normalized displacement function for the joint PMUT design of FIG. 2. A large magnitude 20 cycle drive $V_d(t)$ was applied so that the joint PMUT response is in deep compression departing markedly from a 2n d order linear transfer function model. Further, in FIG. 6, there is no attempt at ring-down mitigation or utilization of $V_{RO}(t)$ signal.

Referring to FIG. 6, let the transmit period $t \leq T_{TX}$, be denoted Tx 610, and let the receive period 640 be the time between transmissions. Let $A_R$ 620 be defined as the maximum displacement amplitude during transmission period $T_X$. Let the ring-down displacement response 630, and its associated blind-zone 635, $T_{TX} < t \leq T_{BZ}$, be defined as beginning at the start of reception and ending at the decay of $e^{-1}$- or −8.7 dB of the displacement amplitude envelope peak $A_R$ during transmission. In this example, in the absence of any ring-down mitigation, the transmission waveform $V_d(t)$ comprised 20 cycles at 1 MHz, resulting in a blind zone period of 38.8 micro-seconds.

Another motivation for the embodiment of FIG. 2 is PMUT transfer function sensitivity and non-linearity with respect to DC bias for ferroelectric piezoelectric materials such as lead zirconate titanate (PZT). The PMUT transfer function is also sensitive to the transverse piezoelectric coefficient, and dielectric constant, which have variance during PMUT fabrication.

The PMUT's resonant frequency and magnitude can also depend on external pressure if the PMUT membrane is coupled directly to the external medium with non-ideal impedance matching. In PMUT applications such as a fingerprint sensor 101 or external body scanner 102, FIG. 1, the skin external pressure 106 is variable introducing uncertainty in the prediction of the ring-down response.

Another challenge is the PMUT's temperature dependent characteristics. During local or external heating, the PMUT's Q factor, an estimate of the resonant frequency magnitude to spectral width, is markedly non-linearly with temperature.

PMUT variation during fabrication both individually and across an array of PMUTs also introduce uncertainty. Small variations in PMUT layer geometry and membrane support can induce residual stress with initial buckling reducing PMUT transmitting sensitivity. For PMUT arrays the fabrication variations can result in a change of resonant frequency between adjacent PMUTs on the order of 1%. The result is an increase in PMUT model parameter uncertainty. While external calibration can be used to estimate PMUT parameters, it is not practical and cost effective at scale.

The full-duplex PMUT design of FIG. 2 bypasses the challenge of prediction in non-linear regimes in the presence of system model and parameter uncertainties. Methods including feedback circuits disclosed below to exploit full duplex simultaneous measurement of actual membrane displacement, a function of $V_{RO}(t)$, FIG. 2. Methods include closed loop feedback to adaptively modify the transmission and an anti-ring down waveforms to minimize the ring-down period.

Figure 7:
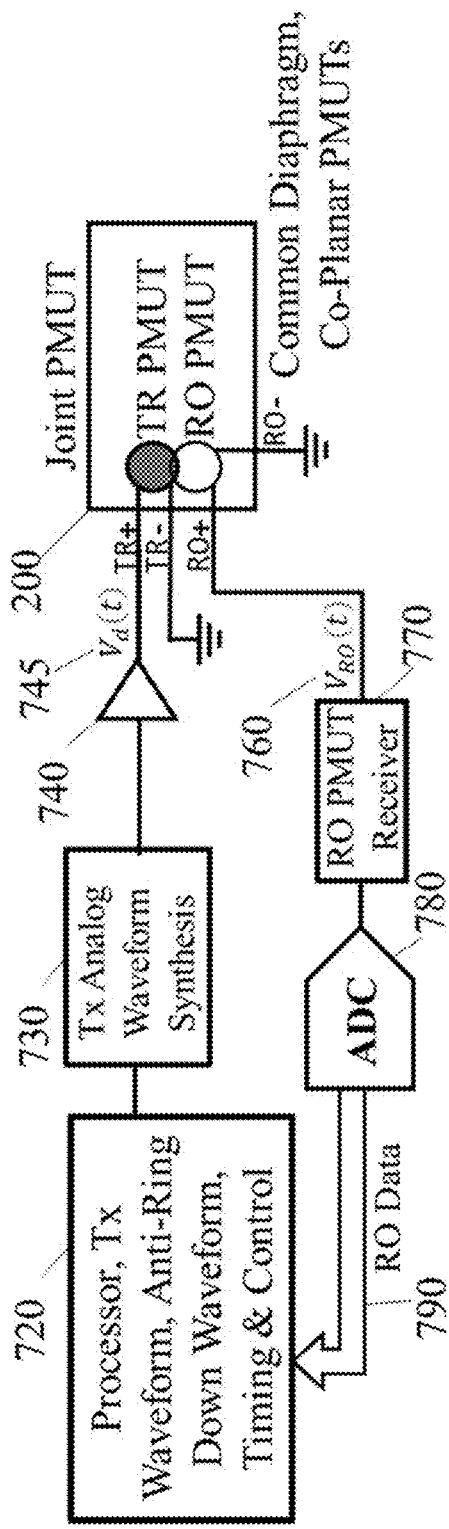
FIG. 7 illustrates exemplary circuit embodiments for full-duplex joint PMUT operation with real-time continuous ring-down suppression.

An illustration of the joint PMUT with transmitter and receiver embodiment endowing full-duplex operation is shown in FIG. 7. During the nominal N cycle and anti-ring-down transmit waveforms, an arbitrary transmit waveform, calculated by processor 720 with analog voltage waveform synthesis 730 drives a high voltage amplifier 740 forming drive voltage $V_d(t)$ 745 coupled to the TR PMUT electrodes of the joint PMUT 200. The voltage across the RO PMUT electrodes constitute the receive waveform, $V_{RO}(t)$ 760 which is coupled to the RO PMUT receiver 770. RO data formed by the receiver and ADC 780 contains sampled estimates, $V_{RO}(t)$, 790 a function of the displacement waveform, across all time including the nominal N cycle transmit cycle, transmitter active anti-ring-down period, as well as the post ring-down, or clean receive period.

Figure 8:
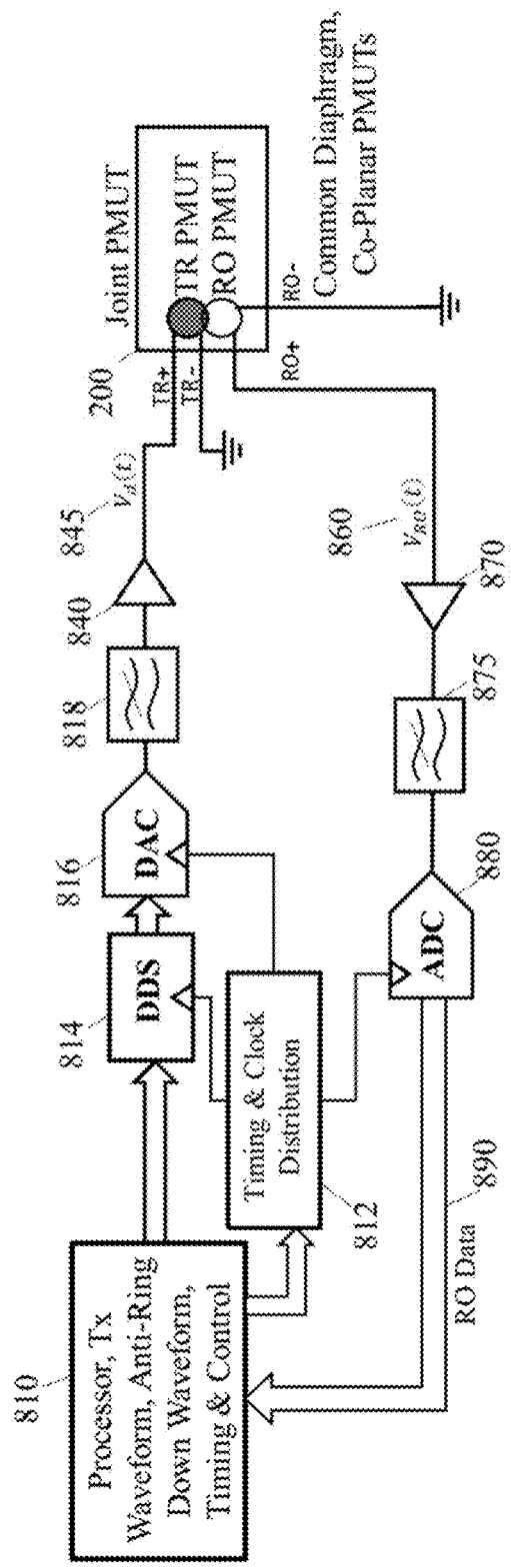
FIG. 8 illustrates exemplary phase coherent circuit embodiments for full-duplex joint PMUT operation with real-time continuous ring-down suppression.

An illustration of a phase coherent embodiment with low pass filtering to permit DC offsets during transmission of the nominal N-cycle waveform as well as transmission of an anti-ring-down waveform is shown in FIG. 8. A transmitter chain starts with real time processor estimation of the transmit waveform 810 utilizing direct digital synthesizer 814, followed by a digital-to-analog converter (DAC) 816 and low pass filter 818. The transmit waveform $V_d(t)$ 845 is obtained after voltage gain with amplifier 840. A common low phase noise reference clock 812 is distributed to both DAC 816, and receiver analog-to-digital converter (ADC) 880.

In FIG. 8 the transmitter independent RO PMUT develops the $V_{RO}(t)$ analog signal 860 continuously across all time, including the nominal N cycle transmit cycle. The signal is amplified by low noise amplifier 870 then low pass filtered 875. Following ADC 880, digitally converted RO data 890 is transferred to processor 810 for real time continuous estimation of optimized transmit waveform as well as transmit anti-ring-down signal. The transmission of an anti-ring-down signal is designed to truncate the receive ring-down period. The processor uses the digitized $V_{RO}(t)$ signal period after the abbreviated ring-down period for close-in time-of-flight detection, ranging, Doppler estimation and imaging.

Figure 9:
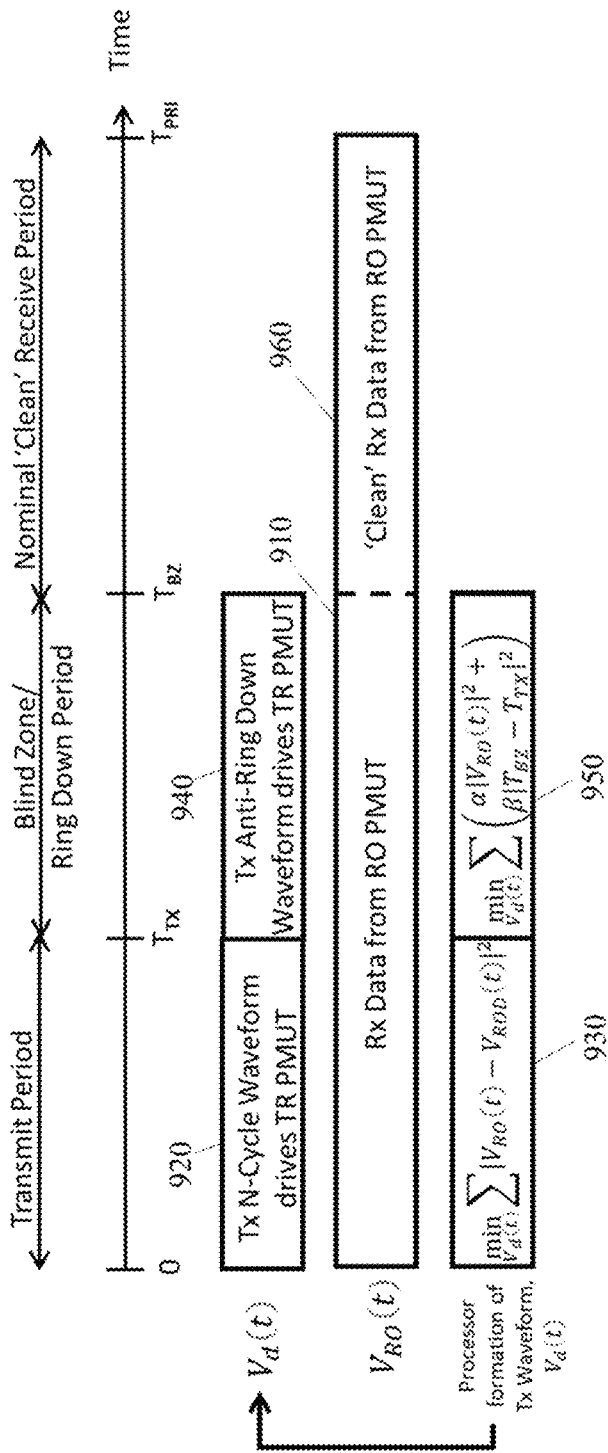
FIG. 9 depicts exemplary methods and timing diagram for transmit waveform optimization and ring-down suppression utilizing feedback from a full-duplex joint PMUT.

One method embodiment of joint PMUT operation to optimize the transmit waveform, and minimize the ring-down duration and residue is shown in the closed loop method of FIG. 9. The RO PMUT develops the $V_{RO}(t)$ analog signal continuously across all time 910 960, including the nominal N cycle transmit cycle. During the nominal N-cycle transmit period, $t \le T_{TX}$ 920, the transmit voltage waveform $V_d(t)$ is optimized by least mean square minimization of an objective function. One objective function 930 is the closed loop estimate of the difference between the received waveform, $V_{RO}(t)$, from the RO PMUT itself a function of the true membrane displacement waveform, $d_{TRUE}(t)$, and a desired receive waveform, $V_{ROD}(t)$, $$\min_{V_d(t)} \sum |V_{RO}(t) - V_{ROD}(t)|^2 \qquad (1)$$

The training function, $V_{ROD}(t)$, is chosen to optimize the Q, bandwidth, resonant frequency, and spectral content of $V_{RO}(t)$. Other forms of the objective function, Eqn (1), include relaxed constraints on the moments and spectral content of $V_{RO}(t)$, as well as matching boundary conditions at $V_{RO}(t)$ at $T_{TX}$, the transition between the nominal N-cycle transmit period and the blind zone period.

Attributes of the desired receive waveform, $V_{ROD}(t)$, can be estimated in real time during the transmit period, or across multiple transmission pulse repetition intervals, in the closed loop feedback for the nominal N cycle transmit waveform, Eqn (1). Components including DC bias, Q, resonant frequency, and harmonic levels calculated in-vivo by analysis of the RO data during the nominal N cycle transmit waveform plus ring-down periods, of total duration $T_{BZ}$.

During the blind zone period, $T_{TX} \le t \le T_{BZ}$ 940, the ring-down residue and blind zone period are minimized by manipulation of $V_d(t)$. One objective function 950, Eqn (2), is the closed loop weighted ($\alpha$, $\beta$) sum of the energy of $V_{RO}(t)$ and the blind zone period duration, $$\min_{V_d(t)} \sum (\alpha |V_{RO}(t)|^2 + \beta |T_{BZ} - T_{TX}|^2). \qquad (2)$$

where $T_{BZ}$ is the time at which a −8.7 dB reduction of the displacement amplitude envelope from its peak as estimated from $V_{RO}(t)$.

Other expressions for the ring-down objective function in Eqn (2) are possible. The first term can itself be a convex sum of the total energy of $V_{RO}(t)$ and the energy of selected spectral components of $V_{RO}(t)$.

Eqns (1) and (2) are minimized in the presence of an unknown non-linear system model and parameter uncertainties. During both the nominal N-cycle transmit and ring-down periods, the transmit voltage waveform $V_d(t)$ optimization is determined by gradient methods and model free reinforcement machine learning methods. The nominal clean receive period 960 commences after the shortened ring down period ends at $T_{BZ}$.

Figure 10:
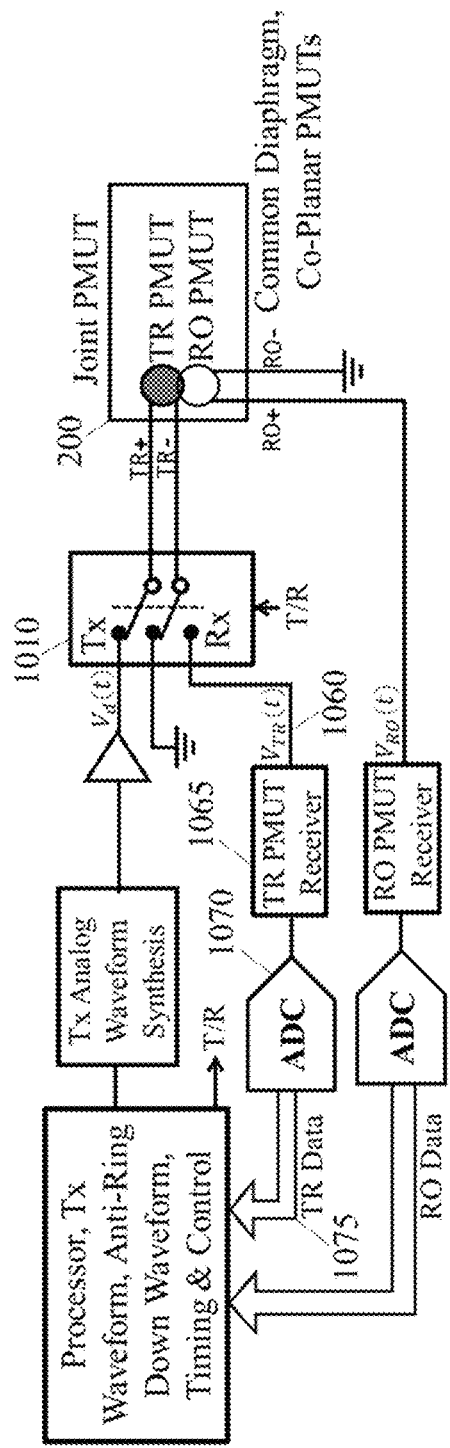
FIG. 10 shows exemplary circuit embodiments for full-duplex joint PMUT operation with independent transmit/receive (TR) and receive-only (RO) PMUT receivers.

Another embodiment, FIG. 10, exploits asymmetric TR and RO PMUT performance in the joint PMUT. The design incorporates an additional dedicated TR PMUT receive chain 1060 1065 1070 1075 enabled by T/R switch 1010. The TR PMUT component was designed for superior sensitivity and noise figure for the clean, post-ring down period, by sacrificing RO PMUT geometry and performance. The RO PMUT and its data are used to optimize the transmit voltage waveform, $V_d(t)$, during both the nominal N-cycle transmit waveform and the ring-down period as well as improve the estimate of the true membrane displacement waveform, $d_{TRUE}(t)$ during the nominal clean receive period. A phase coherent design of the circuit in FIG. 10 is shown in FIG. 11.

Figure 11:
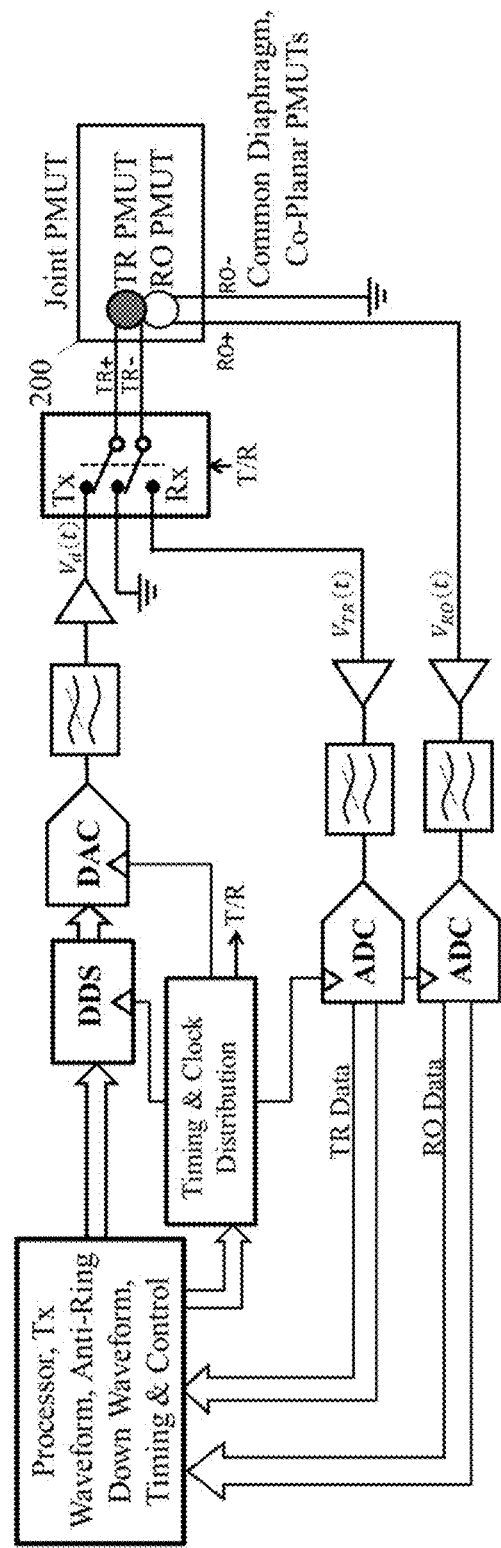
FIG. 11 shows exemplary phase coherent circuit embodiments for full-duplex joint PMUT operation with independent TR and RO PMUT receivers.
Figure 12:
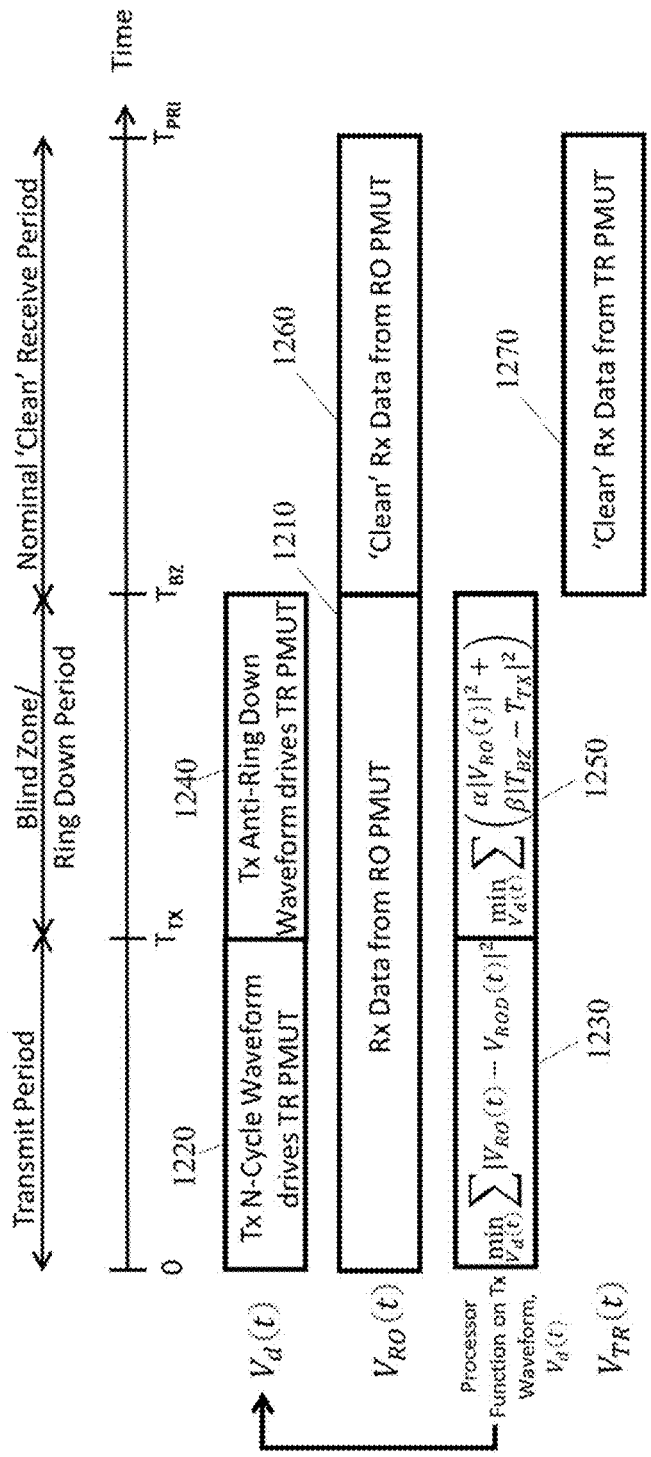
FIG. 12 is exemplary methods and timing diagram for transmit waveform optimization and ring-down suppression for full-duplex joint PMUT with independent TR and RO PMUT receivers.

The joint PMUT operation of FIG. 11 to optimize the transmit waveform 1220 1230 and minimize the ring-down duration and residue 1240 1250 is shown in the closed loop method of FIG. 12. In contrast to the circuit embodiment and method of FIGS. 8 and 9, the TR PMUT's receive data, $V_{TR}(t)$ 1270 13, is heavily weighted relative to $V_{RO}(t)$ 1260 for its superior noise figure, increased sensitivity, and reduced E-field cross-talk with the RO PMUT during the post ring-down or clean receive data period. The closed loop feedback of RO PMUT data 1210 and role is unchanged with optimization of the transmit voltage waveform, $V_d(t)$. Once the transmission and ring-down period are completed the half-duplex switch couples the TR PMUT to the TR PMUT receiver with generation of $V_{TR}(t)$ received data during the clean receive period.

Figure 13:
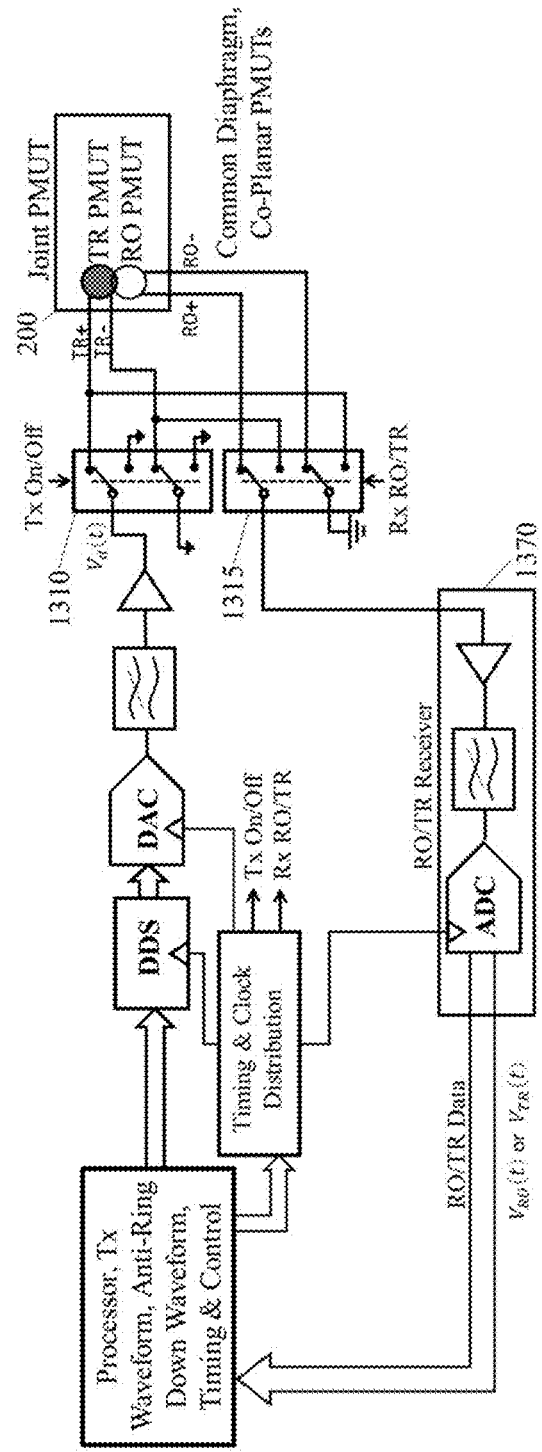
FIG. 13 shows exemplary phase coherent circuit embodiments for full-duplex joint PMUT operation with a single receiver time shared between TR and RO PMUT subcomponents.

Another variant of the embodiment in FIG. 11, time shares a single receiver 1370 between the TR and RO PMUT components of the joint PMUT by double pole single throw switch 1315 as shown in FIG. 13. This circuit utilizes a joint PMUT 200, where the TR PMUT has been designed for superior dynamic range and sensitivity, relative to the RO PMUT. The advantage of this embodiment is a reduction in cost and power consumption of a single receiver compared to the two receiver design of FIG. 11. The sacrifice is the loss of RO PMUT data during the clean receive period.

During the nominal N cycle transmit and ring-down periods, the TR PMUT is coupled to the transmitter and the RO PMUT is coupled to RO/TR Receiver. During the post ring-down or clean data period, by operation of double pole single throw switches 1310 1315, the transmitter is shunted to ground, the TR PMUT is coupled to the RO/TR Receiver, and the RO PMUT is uncoupled. Otherwise, the methods to optimize the transmit voltage waveform, $V_d(t)$, with Eqns (1) and (2) are similar.

Figure 14:
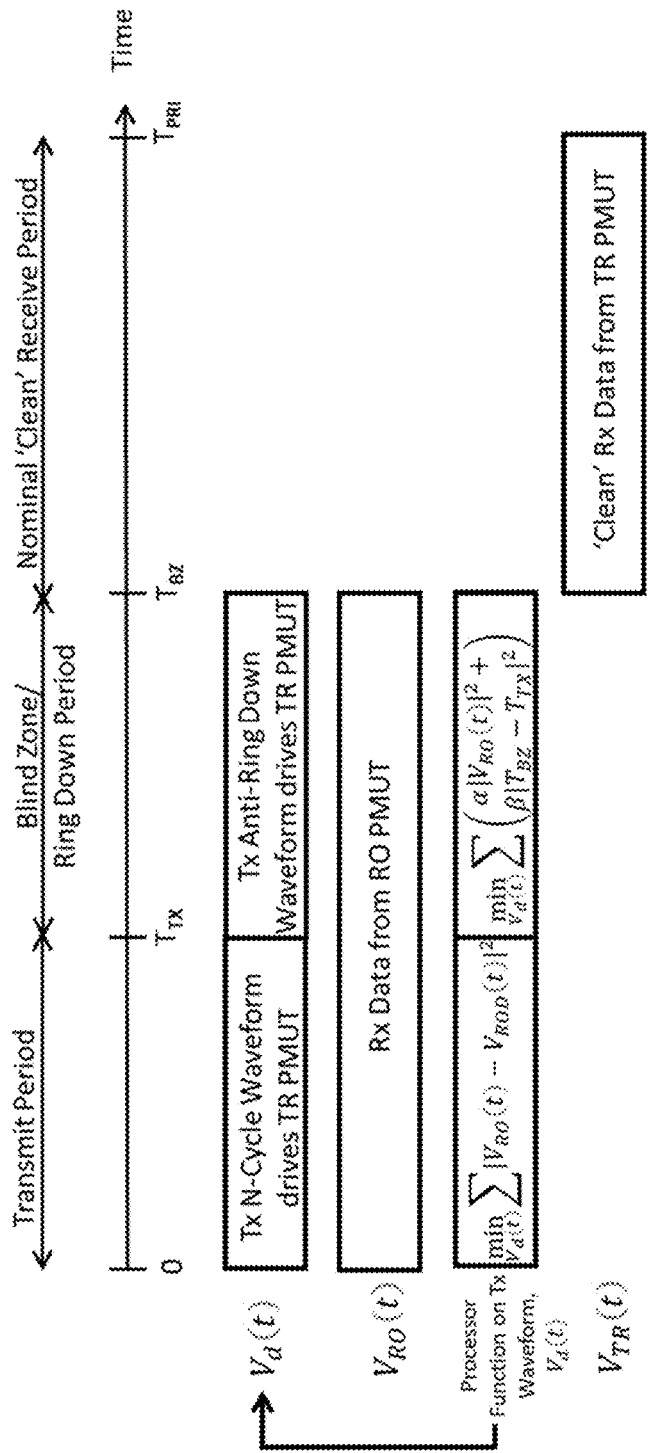
FIG. 14 is exemplary methods and timing diagram for transmit waveform optimization and ring-down suppression for full-duplex joint PMUT operation with a single receiver time shared between TR and RO PMUTs.

One method embodiment for the single receiver design of FIG. 13 is shown in FIG. 14. The RO PMUT is used to optimize the transmit waveform and minimize the ring-down duration and period. Unlike the apparatus embodiment of FIG. 11 and method of FIG. 12, data from only the TR PMUT is used during the post ring-down period.

Figure 15:
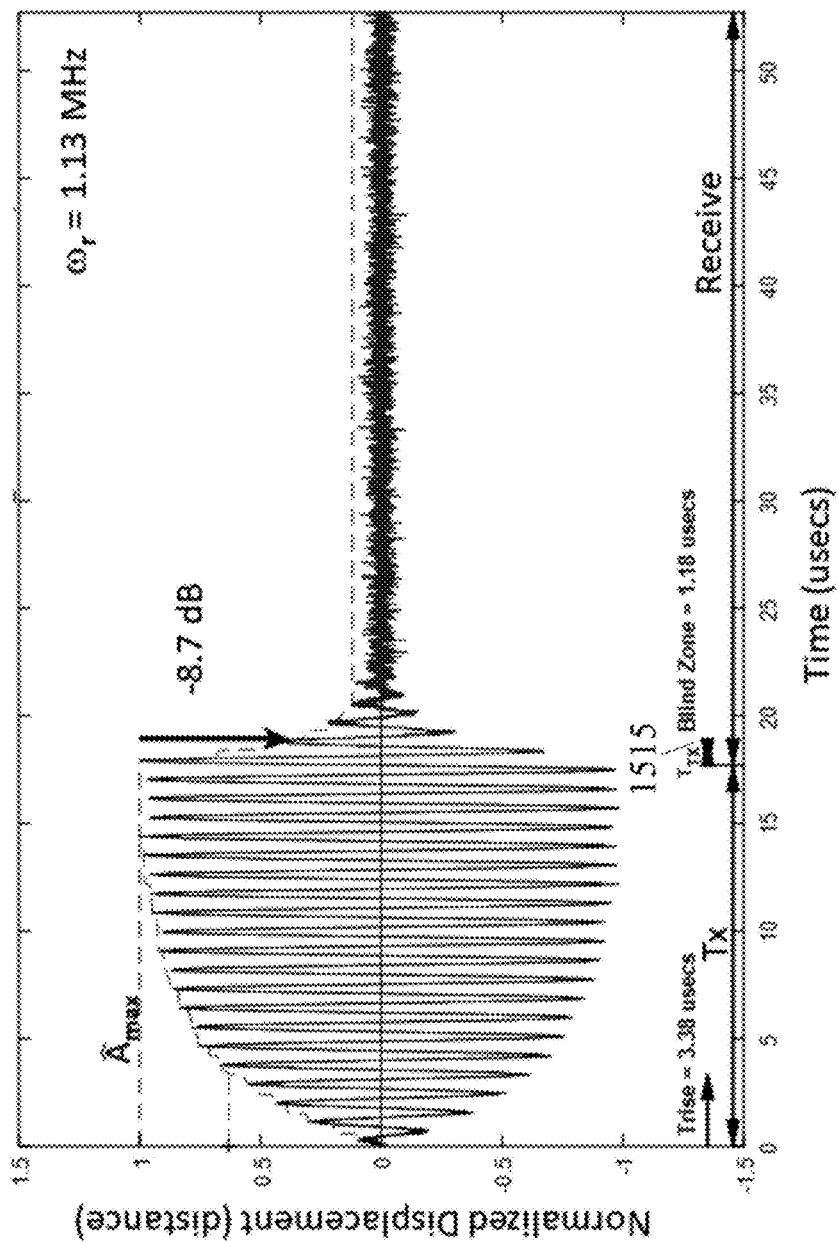
FIG. 15 shows an exemplary time domain displacement response for a full-duplex joint PMUT with feedback control minimizing the ring down period.

FIG. 15 shows the time domain response for the joint PMUT embodiment shown in FIG. 2, with the same large magnitude 20 cycle drive $V_d(t)$ so that the PMUT response was in deep compression during transmission. The closed loop feedback embodiment and methods of FIGS. 13 and 14 optimize the drive voltage, $V_d(t)$, during transmission and ring-down to dissipate the elastic energy abbreviating the ring-down period to 1.2 microseconds 1515.

FIG. 16 quantifies the ring-down performance for an exemplary anti-ring down closed-loop embodiment of the present invention for a joint, co-planar TR RO PMUT apparatus of FIG. 2 and for four open loop methods, no control, PMUT transfer function inversion, PMUT DC bias, and phase shift. The closed loop method utilizes the $V_{RO}(t)$ measurements to optimize the drive voltage $V_d(t)$ during both transmission and ring down using circuit and method embodiments of FIGS. 13 and 14. As shown in the FIG. 16, the closed loop method of the present invention shortens the ring-down/blind zone period by a factor of ~7x-20x relative to the various open-loop methods.

Figure 17:
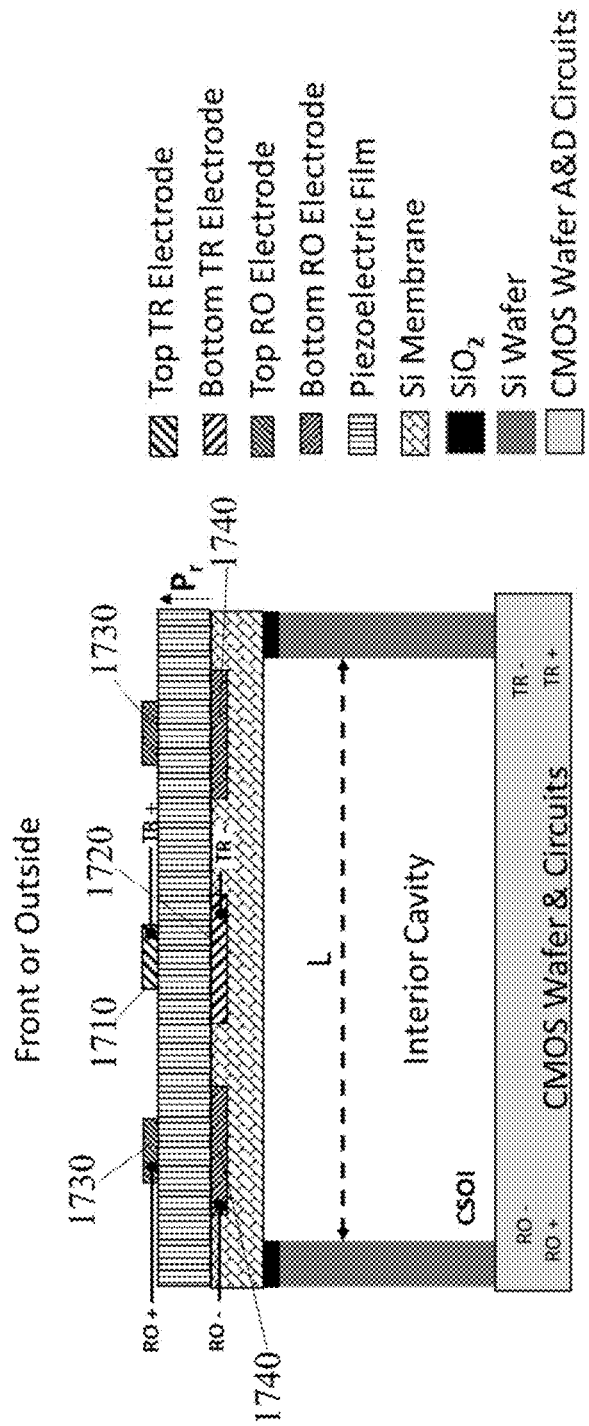
FIG. 17 shows embodiments with a reversal of electrode assignments between TR and RO PMUTs in a joint coplanar position on a common flexible membrane and its components.

There are numerous other embodiments of the joint PMUT design. The designation of the TR and RO components of the joint PMUT may be fixed at design time or be externally switched in real-time. In FIG. 17, not to scale, the TR and RO assignments designations are reversed in contrast with the assignments of FIG. 2. The outer ring-shaped top and bottom electrodes 1730 1740 are associated with the RO piezoelectric sensor and the inner circular disc-shaped top and bottom electrodes 1710 1720 are associated with the TR piezoelectric sensor. Switching the TR PMUT assignment from ring to disc shaped electrodes enables PMUT beamwidth manipulation for imaging; a PMUT with small diameter disc-shaped electrodes has a wider beamwidth compared to a PMUT with larger diameter ring-shaped electrodes.

Figure 18:
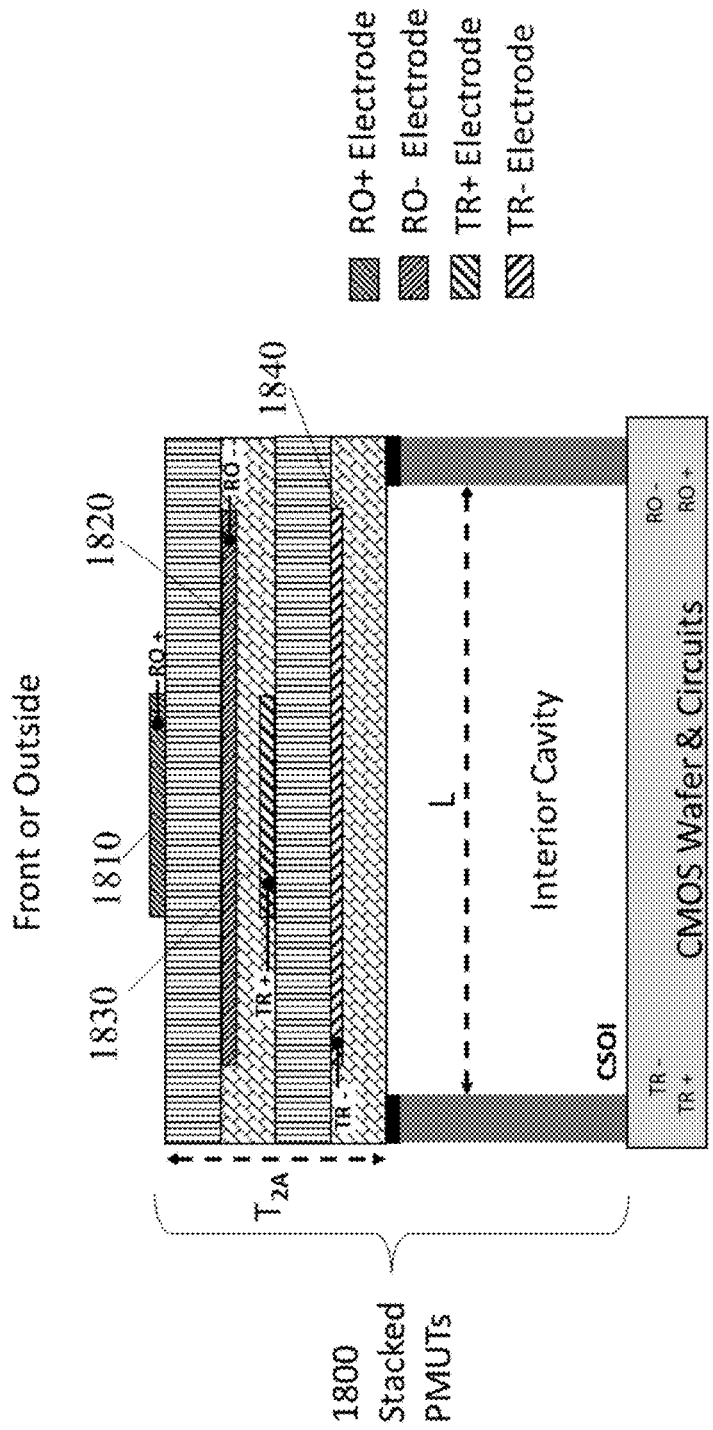
FIG. 18 shows exemplary embodiments of vertical stacking of TR and RO joint PMUT on a common flexible membrane and its components.
Figure 19:
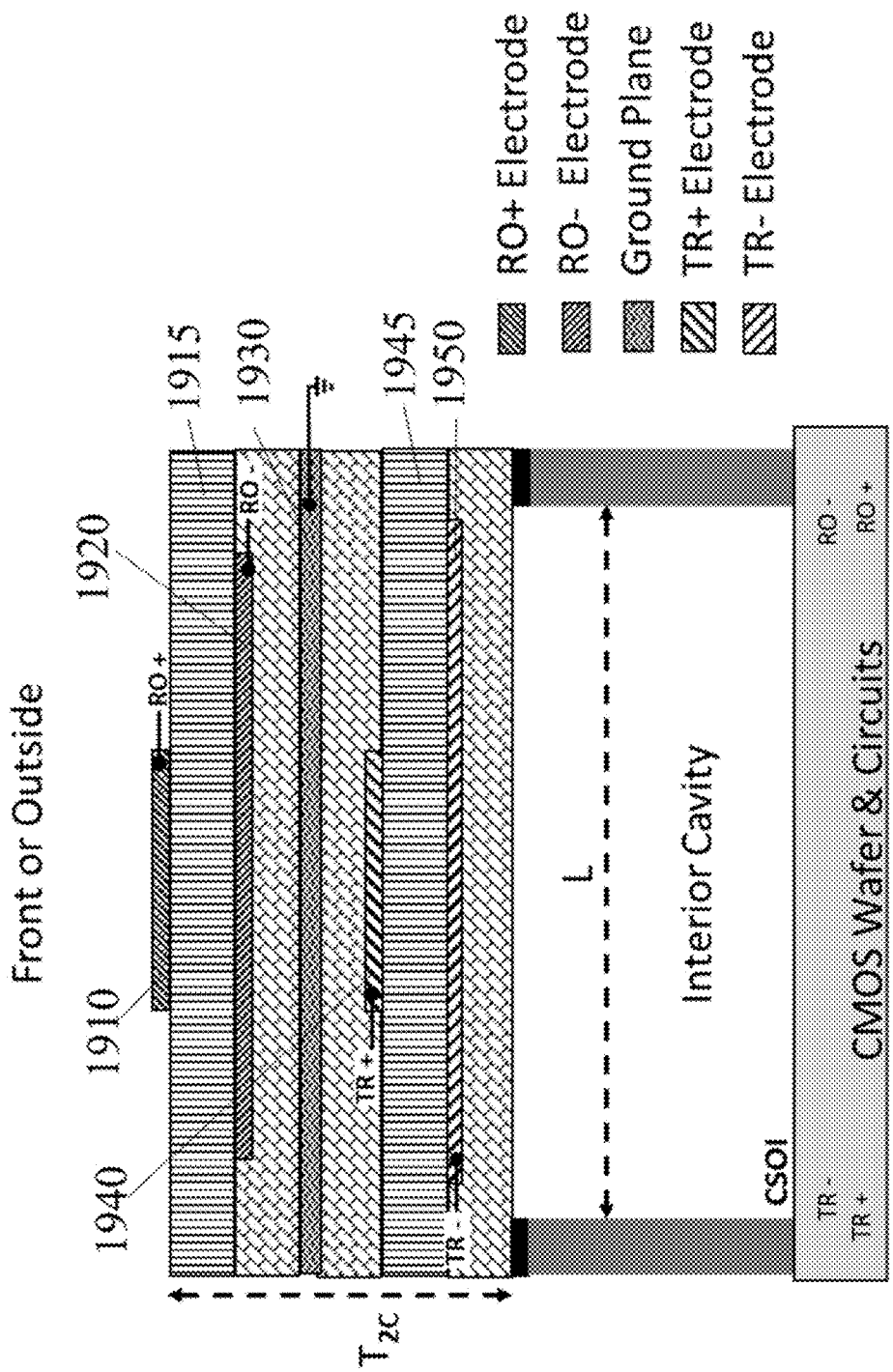
FIG. 19 shows exemplary embodiments with vertical stacking of TR and RO joint PMUT with a separating ground plane to minimize cross-talk on a common flexible membrane.

To reduce E-field cross-talk between TR and RO PMUTs, another embodiment is a vertical stack or layering of the RO and TR PMUTs 1800, FIG. 18, not to scale. The top piezoelectric layer's flexural motion is sensed by an RO electrode pair 1810 1820. The bottom piezoelectric layer is coupled to a TR electrode pair 1830 1840. The stacked film thickness, $T_{2A}$, RO and TR electrode geometries are optimized to both maximize the net Q and minimize electric field cross-talk between TR electrodes and RO electrodes for operation at resonant frequency proportional to $T_{2A} L^{-2}$. FIG. 19, not to scale, illustrates another variant with a ground plane layer 1930 between the top RO PMUT 1910 1915 1920 and bottom TR PMUT 1940 1945 1950 layers to further minimize electric field cross-talk.

Other stacked joint PMUT embodiments are realizable. One example uses a series transduction electrode pair in the shape of a disc and ring located on same side of a piezoelectric layer. A stacked joint PMUT design has a TR PMUT with a bottom disc and ring electrode pair below a piezoelectric layer below a ground plane below another piezoelectric layer topped with a disc and ring electrode pair forming the RO PMUT. This embodiment has the advantage of increased displacement and reduced capacitance, a property of the series transduction electrode pair PMUT design, as well as increased electric field isolation between TR and RO PMUTs.

Figure 20:
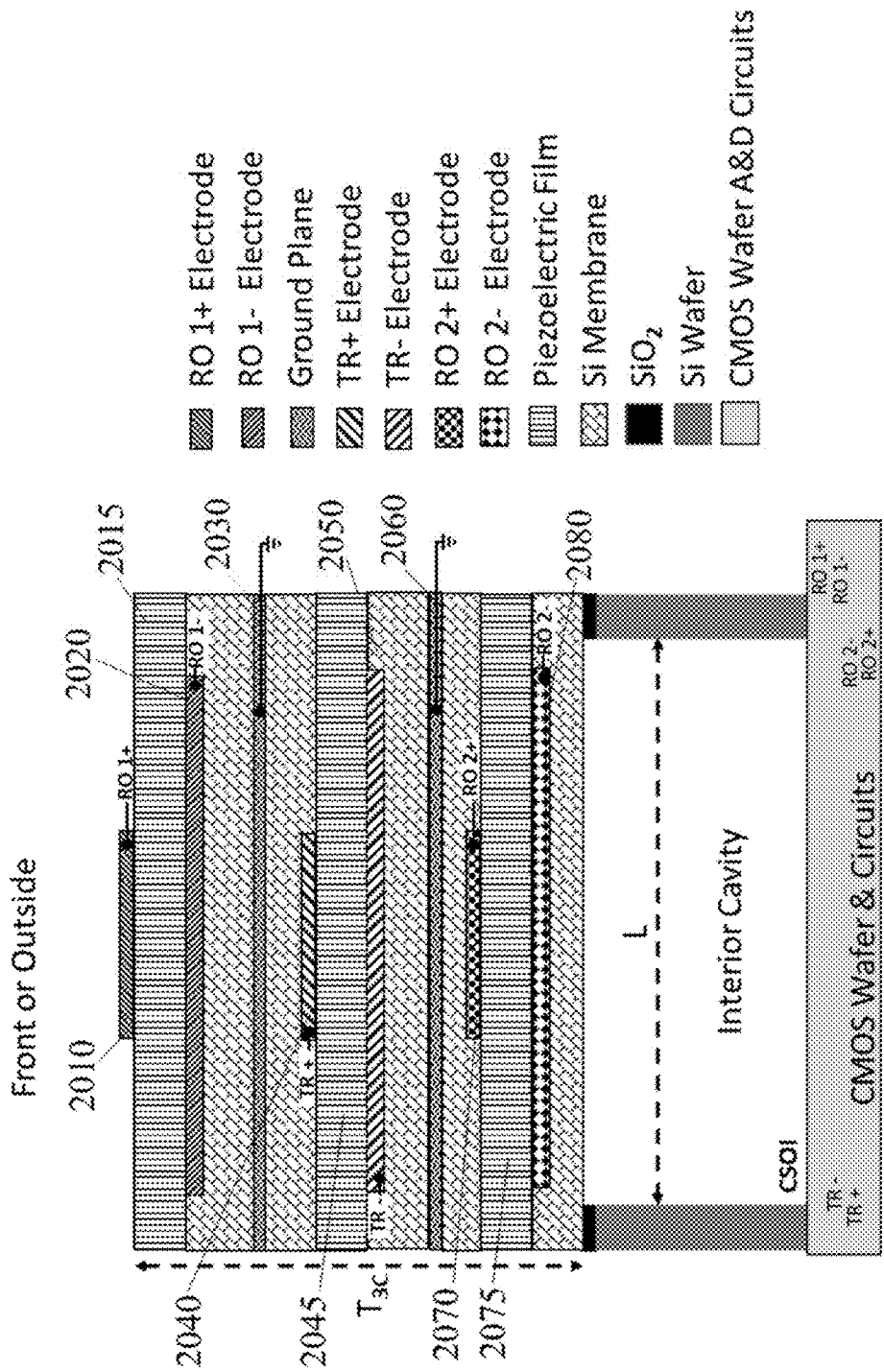
FIG. 20 shows exemplary joint PMUT embodiments of a TR PMUT and two separate RO PMUTs with ground planes and components.

To remove flexural bias between stacked TR and RO components, another joint PMUT embodiment, FIG. 20, not to scale, has a thin film stack composed of three stacked PMUTs. A middle TR PMUT component 2040 2045 2050 is sandwiched between two separate RO PMUT components, RO1 PMUT 2010 2015 2020 and RO2 PMUT 2070 2075 2080 with ground plane layers 2030 and 2060 above and below the TR PMUT component to minimize electric field cross-talk. Functions of the received voltages from the RO1 and RO2 PMUTs are used to cancel the average RO DC bias with respect to relaxed flexion plane of the TR PMUT.

The RO vibration sensor may also be optical. Mechanically coupling an optical sensor to a PMUT transducer has the advantage of high electric field isolation between optical and piezoelectrics, superior sensitivity of the optical sensor to small displacements, with the capacity for high pressure ultrasonic acoustic wave generation by piezoelectric induced membrane flexion.

Figure 21:
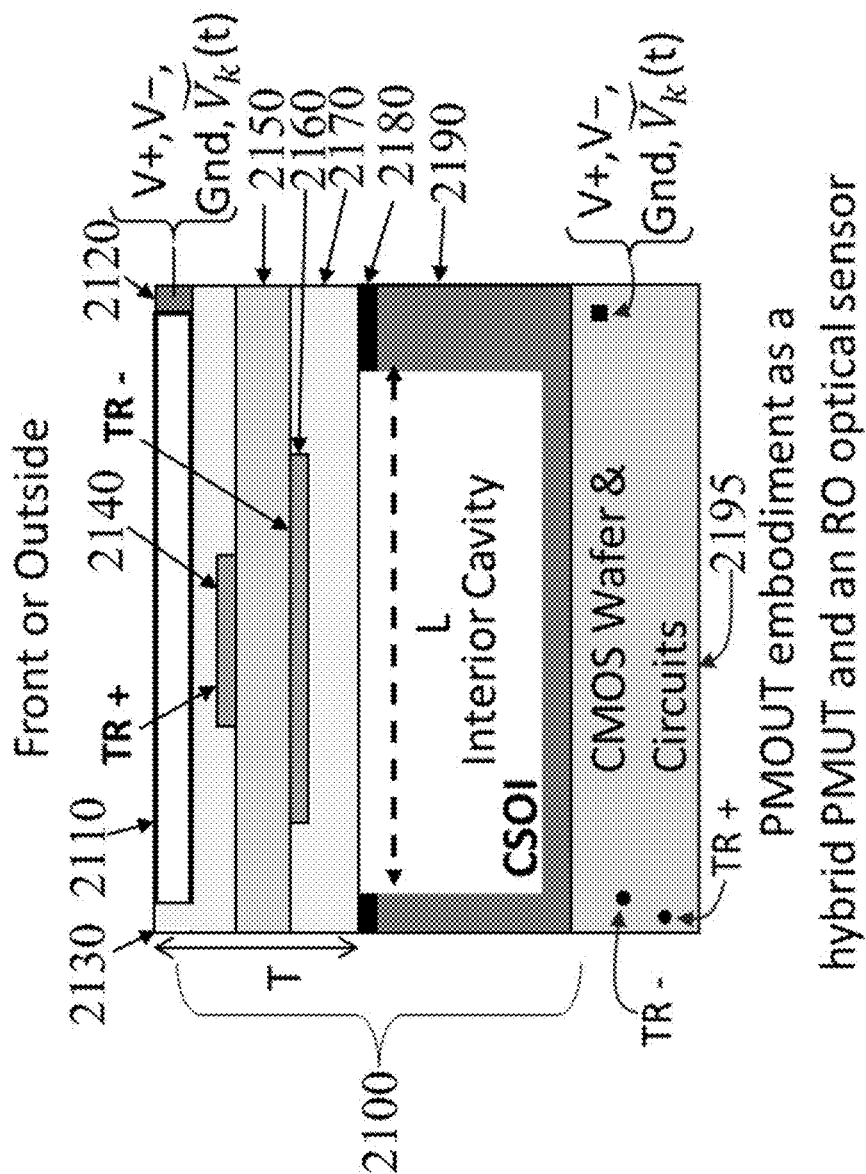
FIG. 21 shows piezoelectric micromachined optical ultrasonic transducer (PMOUT) embodiments as a hybrid TR PMUT and an RO optical sensor and components on a common flexible membrane.

The piezoelectric micromachined optical ultrasonic transducer (PMOUT) is a hybrid TR PMUT and an RO optical sensor. A side view illustration of the PMOUT 2100 is shown in FIG. 21, not to scale. The thin flexible vertical stack of thickness T consists of an RO optical vibration transducer 2110 2120 above a flexible Si layer 2130 above a TR PMUT stack 2140 2150 2160 2170 2180 2190, on a CSOI cavity with diameter L above a CMOS wafer 2195 containing transmitter, receiver, and feedback circuits. The PMOUT resonant frequency is proportional to $T L^{-2}$. The RO optical vibration sensor includes a flexible, square optical waveguide 2110, constructed with guided index materials compatible with modern chip and wafer scale microfabrication techniques. The optical waveguide 2110 and adjacent opto-electronics 2120 are formed on a flexible Si film layer 2130. The stack of flexible optical waveguide and TR A top view of the PMOUT is illustrated in FIG. 22, not to scale.

Figure 22:
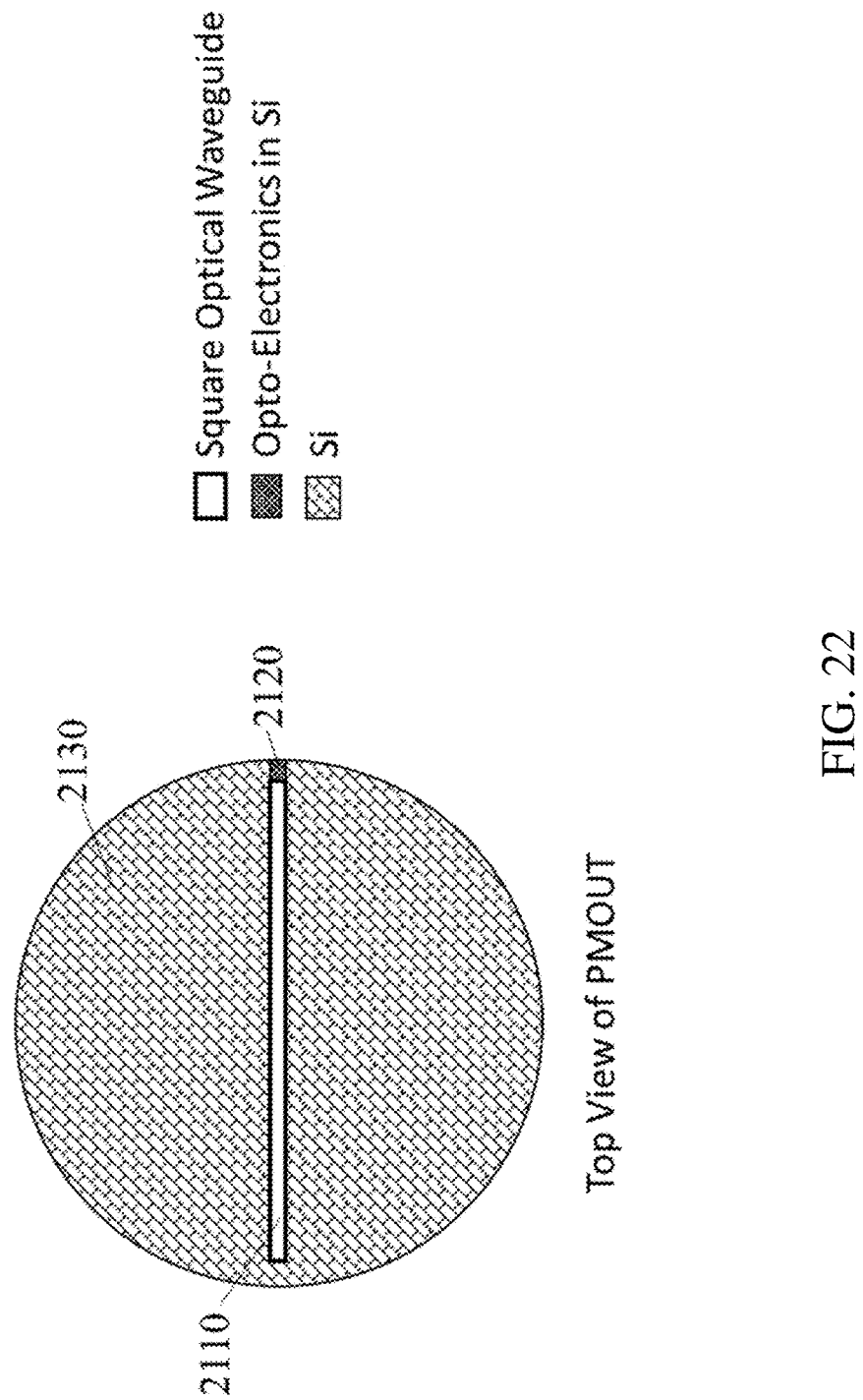
FIG. 22 shows a top view of exemplary PMOUT embodiments and components thereof.
Figure 23:
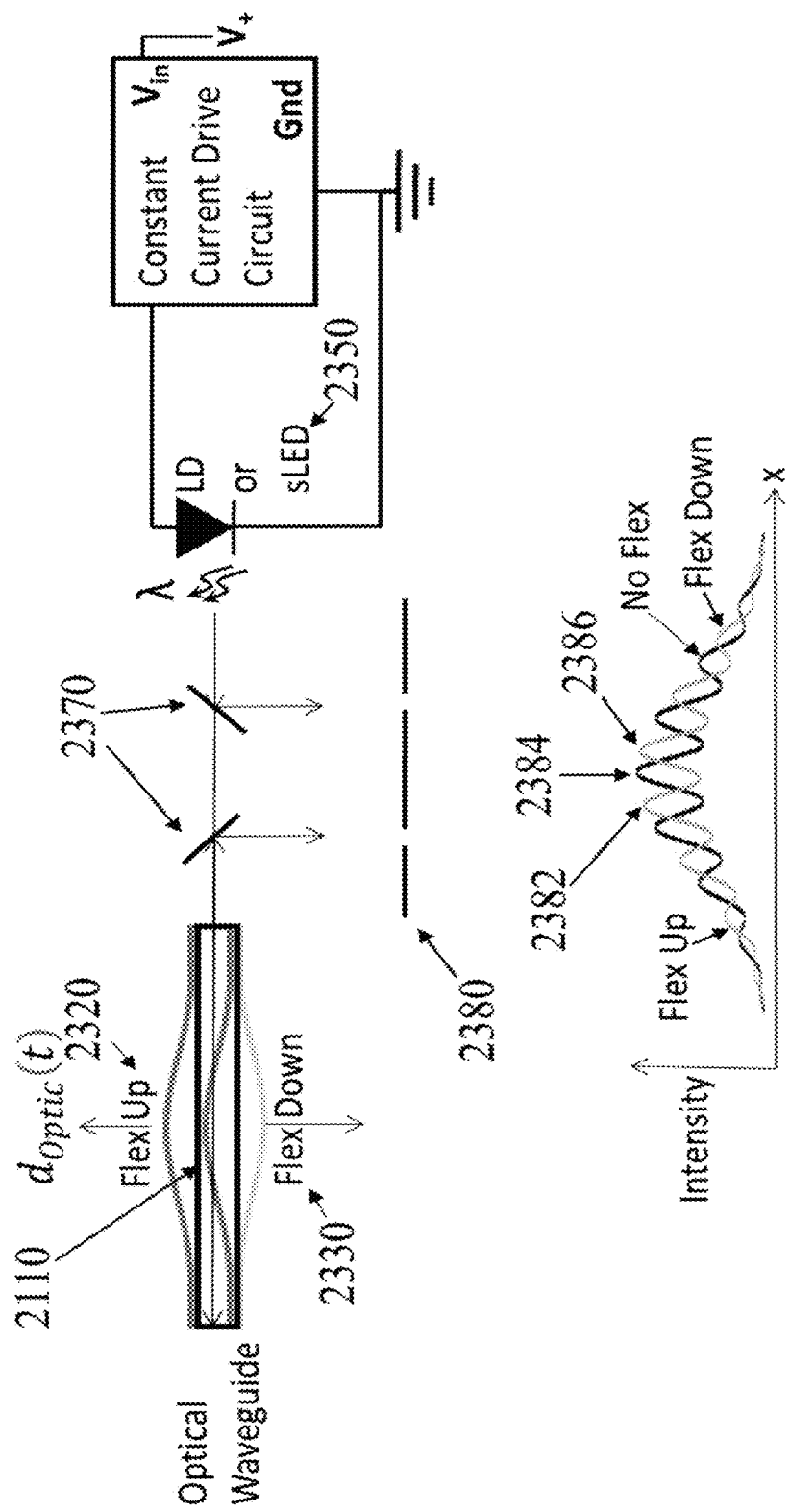
FIG. 23 shows exemplary opto-electronic embodiments including a RO optical sensor and its components.

An example embodiment of optical vibration sensor system compatible with the layout shown in FIGS. 21 and 22 is shown in FIG. 23, not to scale. A low-cost light source with high spatial coherence, such as a laser diode (LD) or super luminescent light emitting diode (sLED) 2350, illuminates a beam splitter 2370. The light passing through the beam splitter is coupled into a square optical flexible waveguide 2110 with sufficiently large numerical aperture. The flexible optical waveguide is itself a stack of dielectric layers, suitable for low-cost wafer-scale large volume fabrication. The light travels across the waveguide, reflects at the distal end due to the refractive index boundary, and returns to be partially reflected at the beam splitter. The beam split reflected light passes through a two slit barrier 2380 resulting in a stable spatial interference pattern with sinc function intensity distribution 2384.

When the optical waveguide is stationary, the spatial interference pattern is stable. When the waveguide is flexed upward 2320 or downward 2330, the phase and illumination center of the light source is translated across the slits. The result is a shift and amplitude change in the spatial interference patterns for 2382 upward flexion, and 2386 for downward flexion.

Figure 24:
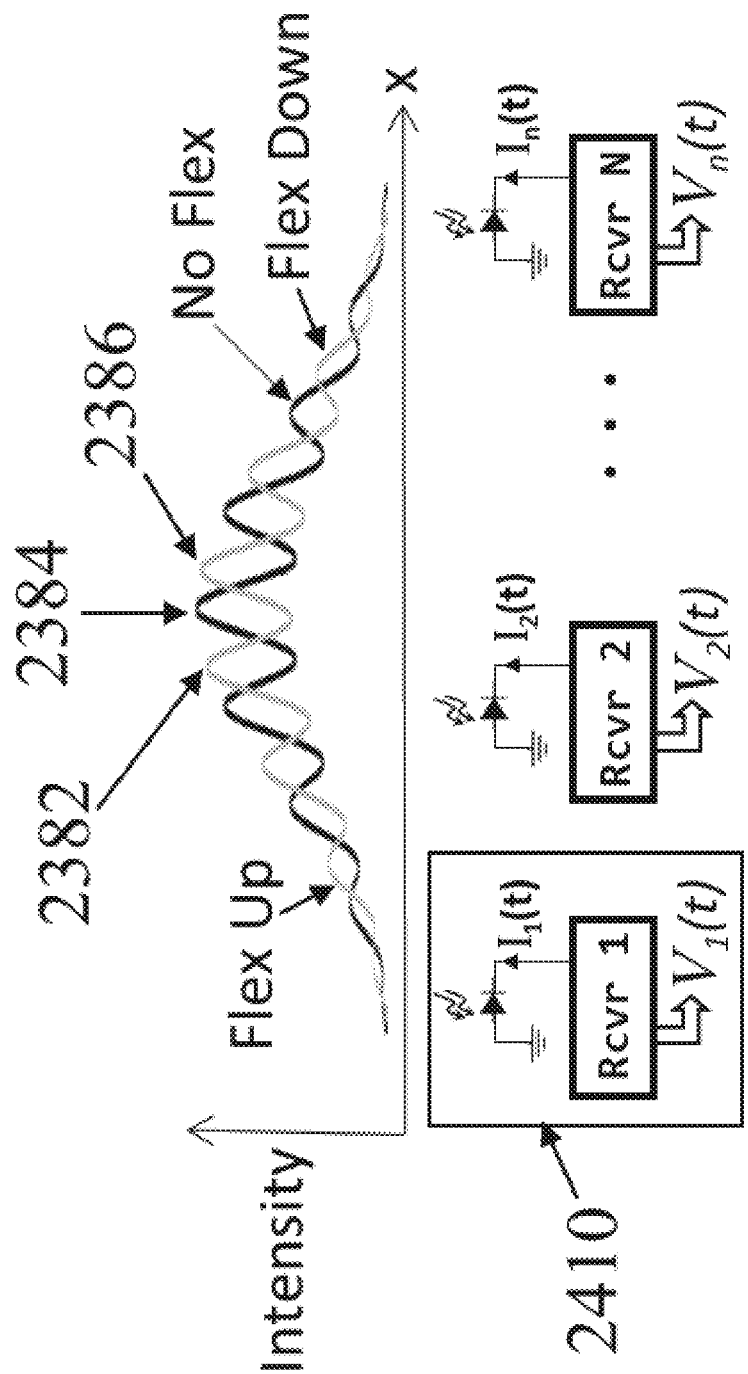
FIG. 24 shows an exemplary spatial sampling of optical interference pattern intensity profile with a photodiode array.
Figure 25:
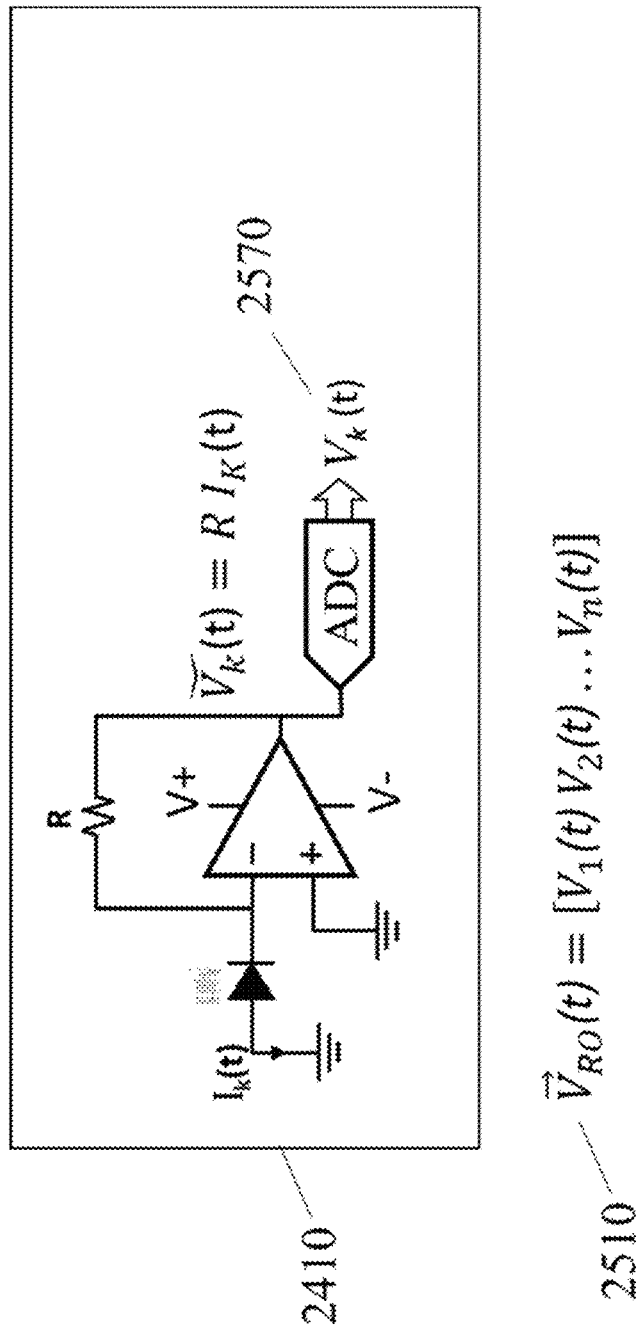
FIG. 25 shows exemplary optical receiver circuits and digital vector formation of interference pattern intensity profile.

FIG. 24, not to scale, illustrates the sampling of the intensity distribution to generate a vector of intensity measurements of the interference pattern. The interference pattern light intensity is spatially sampled at Nyquist or higher frequencies by an array of photodiodes, receivers, and ADCs 2410, FIG. 25, forming a digital vector of light intensities 2510. The array of photodiodes is proximate to the double slit in the opto-electronics area 2120, while the remaining circuits including ADCs are located in the bottom CMOS wafer 2195. The optical circuit geometry, including optical wavelength, waveguide dimensions, slit widths, slit gap, and distance to photodiode array are selected to optimize sampling of the interference pattern on an axis parallel to the double slit. In other embodiments, it may be desirable to perform optical time of flight measurements using a modulated optical signal.

Multiple ADCs may be realized as a single time multiplexed ADC to reduce component count and cost. The optical circuits and signal routing are suitable for low-cost volume production with low-cost dry etch fabrication techniques.

The n-element photodiode array and receiver circuits witness optical waveguide flexions. When n=1, the presence of optical waveguide flexion is witnessed as an AM voltage in $V_{RO}(t)$ 2510. For n>1, $\vec{V}_{RO}(t)$ is the vector of AM voltages corresponding to the intensity spatial distribution across spatial dimension x; a function of both the flexion magnitude and phase of the waveguide displacement waveform d optic (t), $$V_{RO}(t) = f_{Optic}(d_{Optic}(t)) \quad (3)$$

Figure 26:
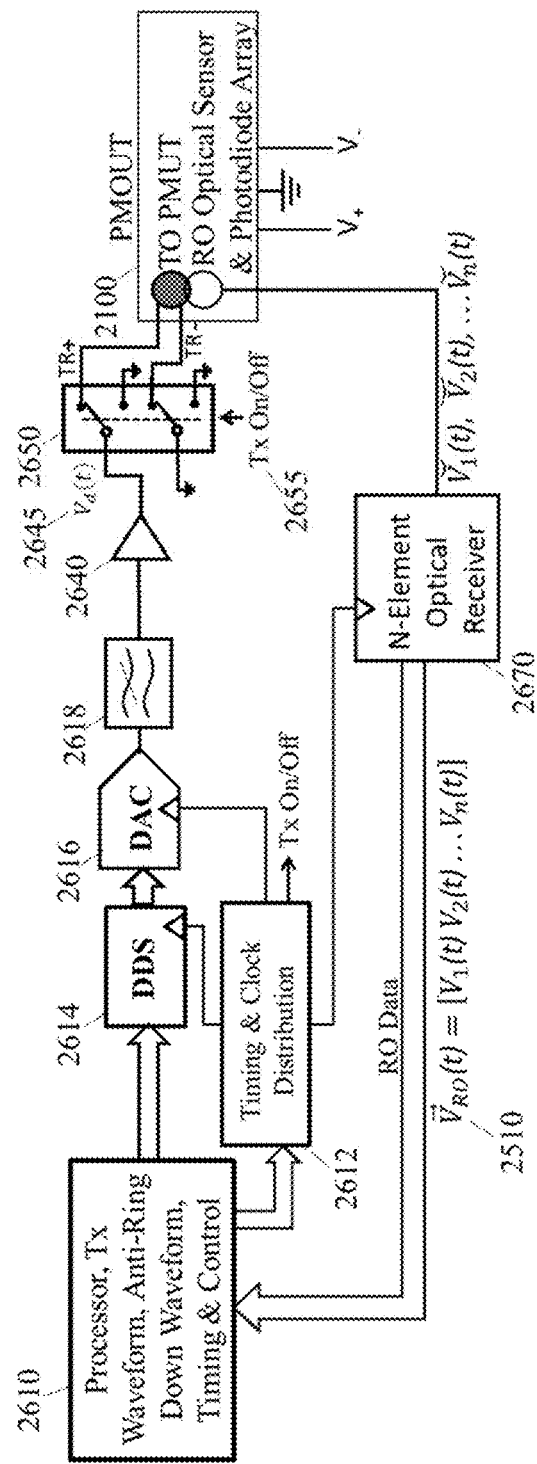
FIG. 26 shows exemplary circuit embodiments for full-duplex joint PMOUT operation.

An example embodiment of the system design for a simplified PMOUT comprise a single transmit only PMUT, or TO PMUT, and a single RO optical sensor is illustrated in shown in FIG. 26. The processor 2610 in the feedback loop optimizes the drive voltage, $V_d(t)$ 2645 with objective functions for the transmission period, $$\min_{V_d(t)} \sum \left| g(\vec{V}_{RO}(t)) - d_{ROD}(t) \right|^2, \, t \leq T_T \quad (4)$$

and ring-down period, $$\min_{V_d(t)} \sum \left( \alpha \left| g(\vec{V}_{RO}(t)) \right|^2 + \beta |T_{BZ} - T_{TX}|^2 \right), \, TTX < t \leq TBZ, \quad (5)$$

where $g(\vec{V}_{RO}(t))$ is an inversion of (3) to estimate the scalar $d_{Optic}(t)$ waveguide displacement waveform from the spatial vector of intensities, and $d_{ROD}(t)$ is the desired, or training, waveguide displacement function.

The transmission chain is comprised of a direct digital synthesizer (DDS) 2614, followed by a DAC 2616 and low pass filter 2618. The transmit and ring-down waveforms $V_d(t)$ 2645 is formed after voltage gain with amplifier 2640. A common low phase noise reference clock is distributed 2612 to both DAC 2616 and ADCs inside the N-element optical receiver 2670. During transmission and ring-down the PMOUT's top 2140 and bottom 2160 TO electrodes are coupled, by switch 2650, to $V_d(t)$ 2645. After ring-down, the PMOUT's TO electrodes are open circuited from $V_d(t)$ by switch Tx On/Off switch control 2655. The RO optical sensor operates continuously forming a vector stream of analog voltages, $\check{V}_1(t), \sqrt{\check{V}_2(t)}, \ldots \check{V}_n(t)$ 2660, which are converted by the n-element optical receiver to digital vector, $\sqrt{\vec{V}_{RO}(t)}$ 2510. In the clean, or post-ring down period, the $\vec{V}_{RO}(t)$ is transferred to processor 2610 for time-of-flight detection, ranging, Doppler estimation and imaging.

Figure 27:
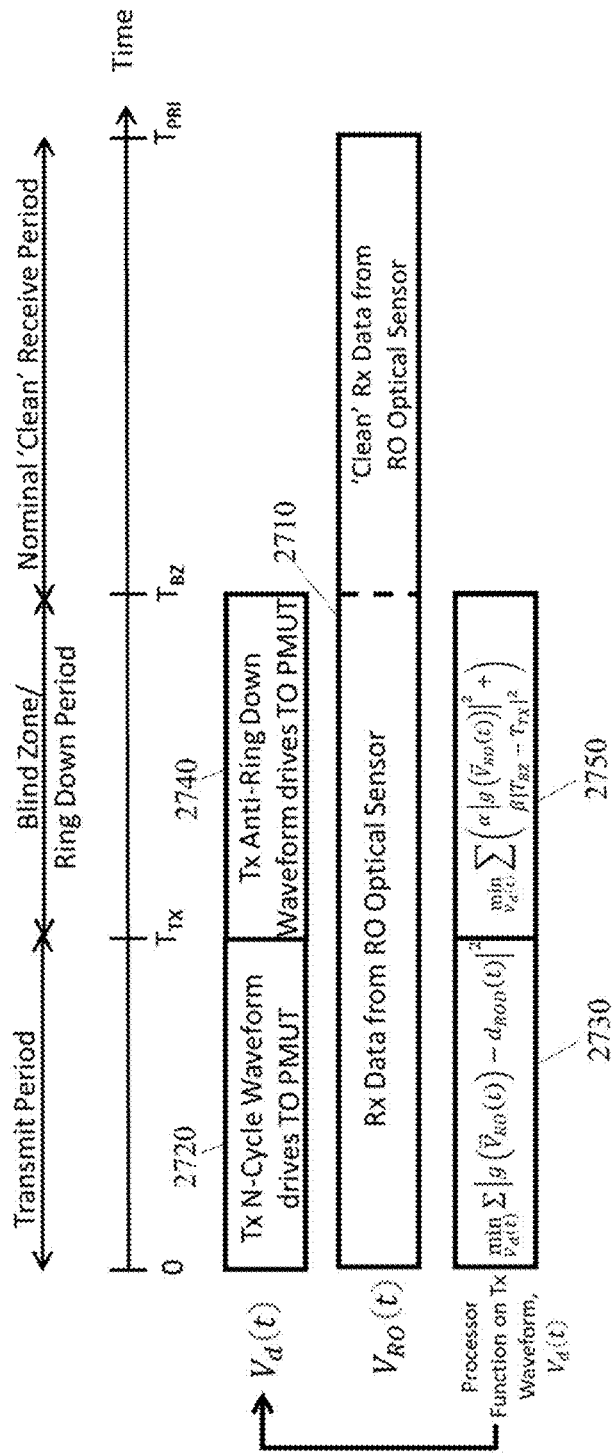
FIG. 27 is an exemplary timing diagram for transmit waveform optimization and ring-down suppression for full-duplex joint PMOUT operation.

One embodiment of the operational methodology is shown in FIG. 27, whose operation is similar to that shown in FIG. 9 which employed an RO PMUT instead of an RO optical sensor. The RO optical sensor provides data across all time including during the nominal N cycle transmit cycle, transmitter active anti-ring-down period, as well as the post ring-down, or clean receive period 2710.

During the transmit n-cycle waveform period 2720, the transmission waveform $V_d(t)$ is optimized in continuous real time by minimization of the error between the observed and desired estimates of the waveguide displacement waveform 2730. During the ring-down period $T_{TX} < t \leq T_{BZ}$ 2740, the transmission waveform $V_d(t)$ is optimized by minimization of weighted ($\alpha$, $\beta$) sum of the energy of waveguide displacement waveform $g(\underline{V}_{RO}(t))$ and the blind zone period duration 2750.

Other embodiments on the above apparatuses and methods will be apparent to those skilled in the art.

During normal echo-location and imaging, PMOUTs systems, and arrays of PMOUTs, have improved close range detection performance, improved dynamic range, improved sensitivity, improved detection, reduced side-lobe levels after matched filtering, increased frequency discrimination, and increased contrast during imaging. These attributes are due to transmit control of the displacement waveform's Q and bandwidth with reduced uncertainty, with reduced ring-down artifact energy and blind zone period reduction. On receive, the PMOUT's optical sensor's superior sensitivity endowed in part from phase changes at optical wavelengths modulating the intensity profile FIG. 23, and dynamic range allow more visibility of weak targets in the presence of strong target returns.

The RO optical sensor may also be comprised of a plurality of optical waveguides at different orientation angles and shapes, such as circular or spiral, to sense different bending characteristics or surface modes in the stacked vibrating membrane. Detecting and measuring the presence of non-unimorph bending characteristics increases the number of observable variables in the feedback control system further reducing uncertainty in the transmit waveform.

For a geographically diverse array of PMOUTs, a subset of the PMOUTs may be used for transmission only. The complementary set of PMOUTs are used for receive only. The PMOUTs simplify the troublesome external array calibration problem with the built-in closed loop feedback circuit of each PMOUT improving bistatic detection and imaging.

The foregoing disclosure provides examples, illustrations and descriptions of the present invention, but is not intended to be exhaustive or to limit the implementations to the precise form disclosed. Modifications and variations are possible in light of the above disclosure or may be acquired from practice of the implementations. These and other variations and modifications of the present invention are possible and contemplated, and it is intended that the foregoing specification and the following claims cover such modifications and variations.

As used herein, the term component is intended to be broadly construed as hardware, firmware, and/or a combination of hardware and software. It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Various elements of the system may employ various levels of photonic, electrical, and mechanical integration. Multiple functions may be integrated on one or more ASICs or modules.

Processors may range, for example, from general-purpose processors and CPUs to field programmable gate arrays (FPGAs) to application specific integrated circuit (ASICs). Software modules (executed on hardware) may be expressed in a variety of software languages (e.g., computer code), including C, C++, Java™, Javascript, Rust, Go, Scala, Ruby, Visual Basic™ FORTRAN, Haskell, Erlang, and/or other object-oriented, procedural, or other programming language and development tools. Computer code may include microcode or micro-instructions, machine instructions, such as produced by a compiler, code used to produce a web service, and files containing higher-level instructions that are executed by a computer using an interpreter and employ control signals, encrypted code, and compressed code.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more". Furthermore, as used herein, the term "set" is intended to include one or more items and may be used interchangeably with "one or more". Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. An ultrasonic transducing sensor apparatus comprising a receive sensor;
at least one PMUT mechanically coupled to, and electrically isolated from, the receive sensor via a common flexible membrane, the at least one PMUT to transmit an acoustic waveform via the membrane in response to a drive voltage $V_d(t)$ and receive a waveform via the membrane, and the receive sensor to receive waveforms via the membrane and provide a feedback signal based on a received waveform, $V_{RO}(t)$, and
at least one processor configured to provide the drive voltage $V_d(t)$ to the at least one PMUT and modify the drive voltage $V_d(t)$ based on the feedback signal that minimize the sum of the square of the difference between the received waveform, $V_{RO}(t)$, and a desired receive waveform, $V_{ROD}(t)$.

2. The apparatus of claim 1, where the at least one processor is configured to use the feedback signal to modify the drive voltage $V_d(t)$ to shorten the ring-down period of the PMUT.

3. The apparatus of claim 1, where the receive sensor is one of an optical sensor and PMUT operating in receive only mode.

4. The apparatus of claim 1, the at least one PMUT is a transceiver operating in transmit-only mode.

5. The apparatus of claim 1, where the at least one PMUT operates in transmit-only mode and the receive sensor is at least one PMUT operating in receive only mode, $PMUT_{RO}$.

6. The apparatus of claim 1, where the at least one PMUT includes at least two PMUTs.

7. The apparatus of claim 1, where the at least one processor is configured to modify the drive voltage $V_d(t)$ to minimize a difference between the RECEIVED WAVEFORM $V_{RO}(T)$, AND A DESIRED RECEIVE WAVEFORM, $V_{ROD}(t)$.

8. An ultrasonic transducing sensor apparatus compromising
   a receive sensor;
   at least one PMUT mechanically coupled to, and electrically isolated from, the receive sensor via a common flexible membrane, the at least one PMUT to transmit an acoustic waveform via the membrane in response to a drive voltage $V_d(t)$ and receive a waveform via the membrane, and the receive sensor to receive waveforms via the membrane and provide a feedback signal based on a received waveform, $V_{RO}(t)$, and
   at least one processor configured to provide the drive voltage $V_d(t)$ to the at least one PMUT and modify the drive voltage $V_d(t)$ based on the feedback signal, and modify the drive voltage $V_d(t)$ to minimize a closed loop weighted ($\alpha$, $\beta$) sum of the energy of $V_{RO}(t)$ and the blind zone duration.

9. The apparatus of claim 1, where the at least one processor is configured to modify the drive voltage $V_d(t)$ using one of gradient methods and model free reinforcement machine learning methods.

10. The apparatus of claim 1, where the receive sensor is a PMUT operating in receive only mode, $PMUT_{RO}$, where the at least one PMUT and the $PMUT_{RO}$ are physically and electrically separated on the common flexible membrane.

11. The apparatus of claim 10, where the at least one PMUT and the $PMUT_{RO}$ both include positive and negative electrodes and one of the at least one PMUT and the $PMUT_{RO}$ positive and negative electrodes physically surround the other of the at least one PMUT and the $PMUT_{RO}$ positive and negative electrodes.

12. The apparatus of claim 10, where one of the at least one PMUT and the $PMUT_{RO}$ has the positive and negative electrodes shaped as a disk proximate including in the center of the common flexible membrane and the other of the at least one PMUT and the $PMUT_{RO}$ has the positive and negative electrodes shaped as a ring surround the positive and negative electrodes shaped as the disk.

13. The apparatus of claim 1, where the receive sensor is a PMUT operating in receive only mode, $PMUT_{RO}$, where the at least one PMUT and the $PMUT_{RO}$ both include positive and negative electrodes and, the apparatus further includes a switch to enable one set of the positive and negative electrodes to operate as the at least one PMUT and the other set of positive and negative electrodes to operate as the $PMUT_{RO}$ in a first switch position and the one set of the positive and negative electrodes to operate as the $PMUT_{RO}$ and the other set of positive and negative electrodes to operate as the at least one PMUT in a second switch position.

14. The apparatus of claim 1, where the receive sensor is not co-planar with the at least one PMUT.

15. An ultrasonic transducing sensor apparatus comprising
   a receive sensor;
   at least one PMUT mechanically coupled to, and electrically isolated from, the receive sensor via a common flexible membrane, the at least one PMUT to transmit an acoustic waveform via the membrane in response to a drive voltage $V_d(t)$, and
   at least once processor configured to provide the drive voltage $V_d(t)$ to the at least one PMUT and modify the drive voltage $V_d(t)$ based on the feedback signal, where the receive sensor is an optical vibration sensor including an optical waveguide and the received waveform, $V_{RO}(t)$, is based on the physical displacement of the optical waveguide by the common membrane.

16. The apparatus of claim 15, further comprising a photodiode array configured to witness the flexion of the optical waveguide, and
   where the at least one processor is further configured to determine the physical displacement of the optical waveguide from the witnessed flexion based on one of optical time of flight and interference pattern intensity profile measurements.

17. The apparatus of claim 15, where the optical waveguide is one of a plurality of optical waveguides in the optical vibration sensor.

18. The apparatus of claim 15, where the optical waveguide is dry etched into a silicon substrate.

19. The apparatus of claim 15, where the optical vibration sensor is positioned in a plane parallel to the at least one PMUT.

20. A method of operating an ultrasonic transducing sensor apparatus comprising:
   providing an ultrasonic transducing sensor apparatus including
      a receive sensor,
      at least on PMUT mechanically coupled to, and electrically isolated from, the receive sensor via a common flexible membrane, the at least one PMUT to transmit an acoustic waveform via the membrane in response to a drive voltage $V_d(t)$ and receive a waveform via the membrane, and the receive sensor to receive waveform, $V_{RO}(t)$, and
      at least one processor configured to provide the drive voltage $V_d(t)$ to the at least one PMUT and modify the drive voltage $V_d(t)$;
   receiving, via the receive sensor, the received waveform, $V_{RO}(t)$;
   providing the feedback signal based on the received waveform, $V_{RO}(t)$ to modify the drive voltage $V_d(t)$ of the at least one PMUT; and
   modifying, via the at least one processor, the drive voltage $V_d(t)$ based on the feedback signal that minimizes the sum of the square of the difference between the received waveform $V_{RO}(t)$, and a desired receive waveform, $V_{ROD}(t)$.

* * * * *